(12) United States Patent
Intoccia, Jr. et al.

(10) Patent No.: US 9,364,306 B2
(45) Date of Patent: Jun. 14, 2016

(54) IMPLANTABLE MEDICAL DEVICE AND METHOD OF PLACEMENT OF THE IMPLANTABLE MEDICAL DEVICE

(75) Inventors: Alfred P. Intoccia, Jr., Nashua, NH (US); Richard Tah, Framingham, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 352 days.

(21) Appl. No.: 13/612,128

(22) Filed: Sep. 12, 2012

(65) Prior Publication Data
US 2013/0245365 A1 Sep. 19, 2013

Related U.S. Application Data

(60) Provisional application No. 61/533,581, filed on Sep. 12, 2011.

(51) Int. Cl.
*A61F 2/02* (2006.01)
*A61F 2/00* (2006.01)

(52) U.S. Cl.
CPC ............. *A61F 2/0009* (2013.01); *A61F 2/0022* (2013.01)

(58) Field of Classification Search
CPC ............................. A61F 2/0022; A61F 2/0009
USPC ................................ 600/29–32; 128/897–899
See application file for complete search history.

(56) References Cited

U.S. PATENT DOCUMENTS

| | | | |
|---|---|---|---|
| 4,643,169 A * | 2/1987 | Koss | A61F 2/0036 128/DIG. 25 |
| 5,483,976 A * | 1/1996 | McLaughlin et al. | 128/885 |
| 5,722,931 A * | 3/1998 | Heaven | 600/29 |
| 5,782,916 A * | 7/1998 | Pintauro et al. | 623/23.66 |
| 5,996,585 A * | 12/1999 | Migachyov | A61F 2/0022 128/885 |
| 6,056,687 A * | 5/2000 | Polyak et al. | 600/29 |
| 6,200,261 B1 * | 3/2001 | Deininger et al. | 600/29 |
| 7,316,663 B2 * | 1/2008 | Whitmore, III | A61M 27/008 604/8 |
| 8,651,109 B2 * | 2/2014 | Ziv | A61F 2/005 128/834 |
| 2006/0064174 A1 * | 3/2006 | Zadno | A61F 2/2418 623/23.68 |
| 2007/0282161 A1 * | 12/2007 | Ferguson et al. | 600/32 |
| 2009/0247969 A1 * | 10/2009 | Nishtala et al. | 604/328 |
| 2011/0295058 A1 * | 12/2011 | Henriksson et al. | 600/37 |
| 2013/0338431 A1 * | 12/2013 | Shalon et al. | 600/32 |

* cited by examiner

*Primary Examiner* — Navin Natnithithadha
*Assistant Examiner* — Sunita Reddy
(74) *Attorney, Agent, or Firm* — Brake Hughes Bellermann LLP

(57) ABSTRACT

A medical device having a valve member and a securing member is provided. The valve member is configured to be positioned inside a bodily passageway. The valve member includes a plurality of flaps configured to move from a first position to a second position at a predetermined pressure or in response to being exposed to a predetermined pressure. The securing member is configured to be positioned outside the bodily passageway. The securing member is configured to help retain the valve member in place within the bodily passageway.

14 Claims, 26 Drawing Sheets

700

IMPLANTABLE MEDICAL DEVICE AND METHOD OF PLACEMENT OF THE IMPLANTABLE MEDICAL DEVICE

CROSS-REFERENCE TO RELATED APPLICATION

This application is a Nonprovisional of, and claims priority to, U.S. Patent Application No. 61/533,581, filed Sep. 12, 2011, entitled "IMPLANTABLE MEDICAL DEVICE AND METHOD OF PLACEMENT OF THE IMPLANTABLE MEDICAL DEVICE", which is incorporated by reference herein in its entirety.

BACKGROUND

1. Field

The invention generally relates to medical devices and procedures, and particularly to medical devices and methods of disposing medical devices into a patient's body for controlling flow of bodily fluids and substances.

2. Description of the Related Art

Fecal incontinence is a disorder that involves involuntary passage of feces through a patient's anal canal. The disorder may be caused by weakness or damage to internal and external anal sphincters muscles or levator ani muscles surrounding the anal canal of the patient's body. Usually, in a normal human body, the internal and external sphincters and levator ani muscles support a rectum and may help provide the rectum an ano-rectal angle that sustains the feces in the rectum until voluntary defecation. Any damage or weakness in these sphincters or muscles may result into incontinence i.e., loss of regular control of fluids.

Treatment of this problem has been centered on rehabilitation & behavior modification, dietary changes, drugs, and surgical treatments (implants such as artificial sphincters or valves) among others. Among all the methods and procedures, the use of implants, such as artificial sphincters, valves or closure means that occludes a body opening or passageway are well known.

Currently, closing and/or opening of artificial sphincters or valves is regulated by generating a pressure mechanically, electrically or electronically by using external means. The external means are also implanted in a patient's body that increase surgical and post-surgical complications.

Further, the artificial sphincters or valves are supported through frictional force of the bodily tissues within a patient's body. With an increase in the pressure generated by the external means, the possibility of dislocating the sphincter or valve member increases, which may lead to complications and their poor functioning. Therefore, surgical placement of the currently utilized sphincters or valves within the body is not an effective way of securing the sphincters or valves.

Thus, there is a need for a medical device that precludes the need of external means for regulating the flow of the bodily material. Further, a securing device and method for securing the sphincters and valves is required to ensure correct position within the passageway.

SUMMARY

A medical device with a valve member and a securing member is provided. The valve member is configured to be positioned inside a bodily passageway. The valve member includes a plurality of flaps configured to move from a first position to a second position at a predetermined pressure or in response to being exposed to a predetermined pressure. The securing member is configured to be positioned outside the bodily passageway. The securing member is configured to help retain the valve member in place within the bodily passageway.

BRIEF DESCRIPTION OF THE FIGURES

The invention and the following detailed description of certain embodiments thereof may be understood with reference to the following figures.

DETAILED DESCRIPTION

Detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. Further, the terms and phrases used herein are not intended to be limiting, but to provide an understandable description of the invention.

The terms "a" or "an," as used herein, are defined as one or more than one. The term "another," as used herein, is defined as at least a second or more. The terms "including" and/or "having", as used herein, are defined as comprising (i.e., open transition). The term "coupled" or "operatively coupled," as used herein, is defined as connected, although not necessarily directly and mechanically.

In general, the invention is directed to systems, methods, and devices for treating fecal incontinence. However, the invention can be equally employed for other treatment purposes such as urinary incontinence. As described below in various illustrative embodiments, the invention provides systems, methods, and devices employing an improved valve arrangement configured to be implanted within a patient's body for controlling flow of bodily fluids and substances.

The term patient may hereafter be used for a person who benefits from the medical device or the methods disclosed in the present invention. For example, the patient can be a person whose body receives the medical device disclosed by the present invention in a surgical treatment. For example, in some embodiments, the patient may be a human female, a human male, or any other mammal.

Figure 1:
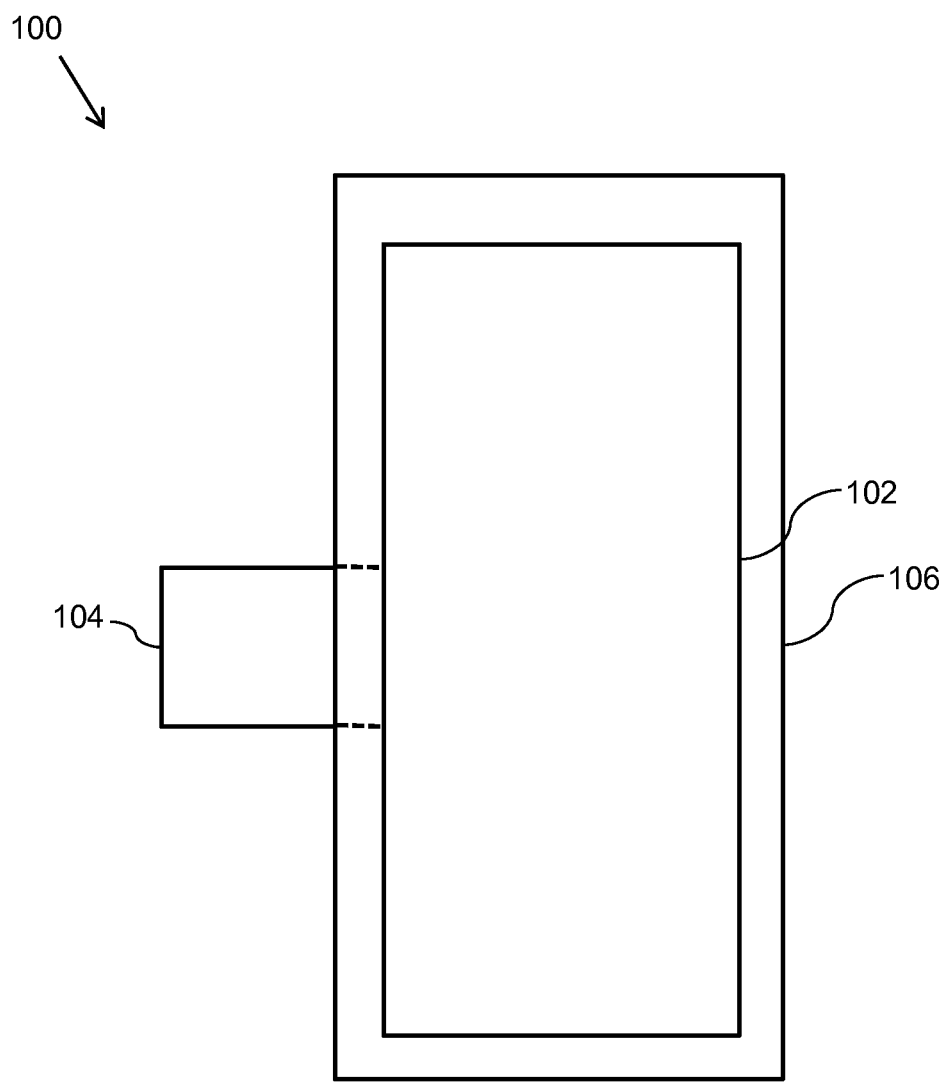
FIG. 1 is a schematic diagram of a medical device configured to be implanted within a patient's body, in accordance with an embodiment of the present invention.

FIG. 1 is a schematic diagram of a medical device 100 configured to be implanted within a patient's body. The medical device 100 includes a valve member 102 and a securing member 104.

The valve member 102 is configured to be positioned inside a bodily passageway 106 such as a urethra, an anal canal, or a rectum of a patient. The valve member 102 includes a plurality of flaps that are configured to move from a first position to a second position at a predetermined pressure or in response to being exposed to a predetermined pressure. In some embodiments, the first position of the plurality of flaps defines a closed configuration of the valve member 102 and the second position of the plurality of flaps defines an opened configuration of the valve member 102.

The predetermined pressure is a threshold cracking pressure that develops due to an accumulated bodily material inside the bodily passageway 106. In some embodiments, the accumulated bodily material can be a fecal material that accumulates inside a patient's anal canal. The weight or pressure of the fecal material generates a downward force causing the development of a pressure which increases with an increase in the quantity of the fecal material. The plurality of flaps move from the first position to the second position when the predetermined pressure is reached within the bodily passageway 106.

In some embodiments, the predetermined pressure depends on the nature and properties of the material and dimensions of the plurality of flaps. Therefore, in some embodiments, the predetermined pressure can be changed by changing stiffness of the material used in the plurality of flaps. In some other embodiments, the predetermined pressure can be changed by changing thickness of the plurality of flaps.

The valve member 102 may include an upper portion, a bottom portion, and a body portion. In some embodiments, the upper portion of the valve member 102 is substantially larger in circumferential area than the bottom portion of the valve member 102. The upper portion of the valve member 102 forms an inlet port for the bodily material flowing through the bodily passageway 106 and the bottom portion of the valve member 102 forms an outlet port for the bodily material flowing through the bodily passageway 106. The valve member 102 includes the hollow body portion between the upper portion and the bottom portion.

In accordance with several embodiments, design of the valve member 102 and the plurality of flaps may vary based on the intended use, and type and severity of the disease for treatment. In some embodiments, the valve member 102 may be substantially oval at its upper portion. In other embodiments, the valve member 102 may be substantially circular at its upper portion. In some embodiments, the bottom portion of the valve member 102 is substantially planar. The bottom portion of the valve member 102 ends with a tip that has almost zero circumferential area. In accordance with various embodiments, a slit is formed at the bottom portion in a second position of the plurality of flaps (opened configuration). The slit allows removal of the bodily material accumulated in the bodily passageway 106 above the valve member 102. The size of the slit formed in the opened configuration may be set or customized based on a patient's requirements.

In some embodiments, the body portion of the valve member 102 that forms a wall section of the valve member 102 is tapered, such as parabolically tapered, and converges toward the bottom portion. In accordance with other embodiments, the tapering body section may follow a profile other than the parabolic profile such as a conical profile.

In some embodiments, the valve member 102 can include two flaps. In other embodiments, the valve member 102 can include more than two flaps.

In some embodiments, the valve member 102 is made of an elastomeric material. Exemplary elastomeric materials are natural polyisoprene, synthetic polyisoprene, polybutadiene, chloroprene, polychloroprene, neoprene, butyl rubber, halogenated butyl rubbers, styrene-butadiene, nitrile rubber, ethylene propylene rubber, epichlorohydrin rubber, polyacrylic rubber, silicone rubber, fluorosilicone rubber, fluoroelastomers, perfluoroelastomers, polyether block amides, chlorosulfonated polyethylene, ethylene-vinyl acetate, thermoplastic elastomers (TPE), elastin, polysulfide rubber, silicones, and the like.

The securing member 104 is configured to be positioned outside the bodily passageway 106 such as the urethra, anal canal, or rectum of the patient. The securing member 104 is configured to help retain the valve member 102 in place within the bodily passageway 106. In some embodiments, the securing member 104 can be tied around the bodily passageway 106 circumferentially such that it can be stretched to a required length to generate a sufficient holding force and retain the valve member 104 in place. In some embodiments, a holding mechanism may be provided on the valve member 102 to retain it in place.

In some embodiments, the securing member 104 can be an elastomeric strip or an elastomeric band. In other embodiments, the securing member 104 can be any kind of a suture. In accordance with various embodiments, the securing member 104 can be made of any elastomeric material. Some of the elastomeric materials that can be used for this purpose have been described above.

Figure 2A:
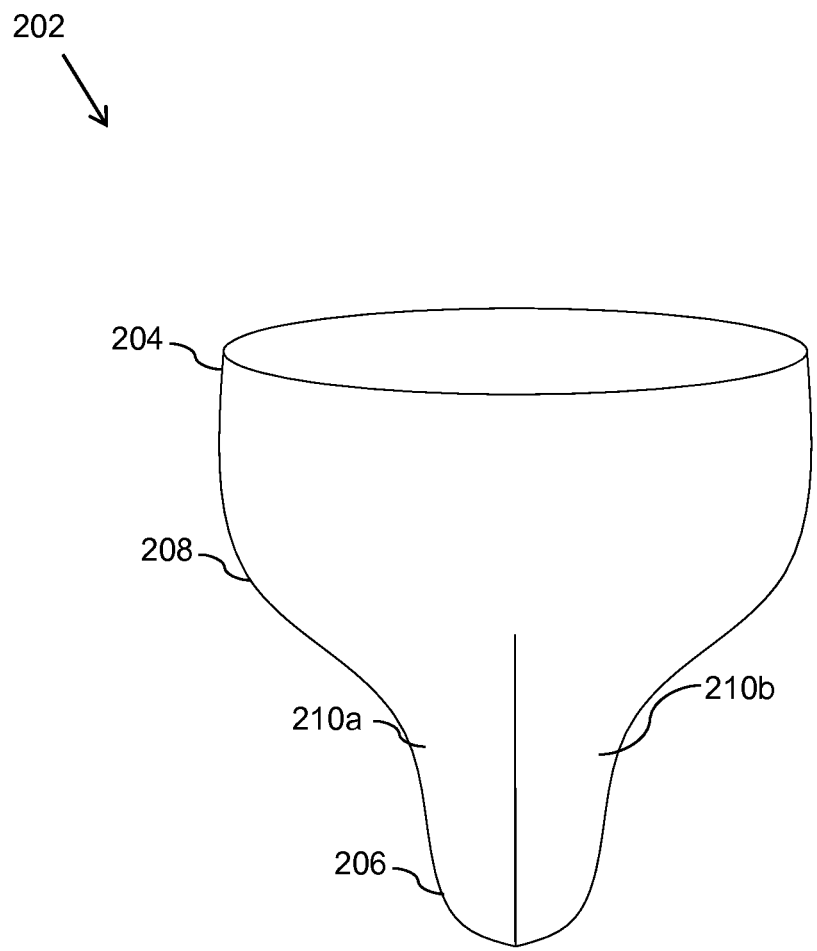
FIGS. 2A and 2B illustrate perspective views of a valve member in closed and opened configurations, respectively, in accordance with an embodiment of the present invention.

FIG. 2A is a perspective illustration of a valve member 202 in a closed configuration, in accordance with an embodiment of the present invention. The valve member 202 includes an upper portion 204, a bottom portion 206, and a body portion (medial portion) 208. The upper portion 204 of the valve member 202 forms an inlet port for a bodily material flowing through a bodily passageway and the bottom portion 206 of the valve member 202 forms an outlet port for the bodily material flowing through the bodily passageway.

As illustrated in FIG. 2A, the valve member 202 includes two flaps (a first flap 210*a* and a second flap 210*b*) that are configured to contact one another when the two flaps 210*a* and 210*b* are at a first position. The first position of the first and the second flaps 210*a* and 210*b* defines the closed configuration such that the flow of a bodily material is restricted in this condition.

The design of the flaps 210*a* and 210*b* and the valve member 202 can be similar to the design of the flaps and the valve member as described in conjunction with FIG. 1. As shown in FIG. 2A, the first flap 210*a* and the second flap 210*b* define a planar configuration toward the bottom portion 206 that comes in contact with one another. The planar end of the first flap 210*a* is configured to contact the planar end of the second flap 210*b* for closing the valve member 202.

Figure 2B:
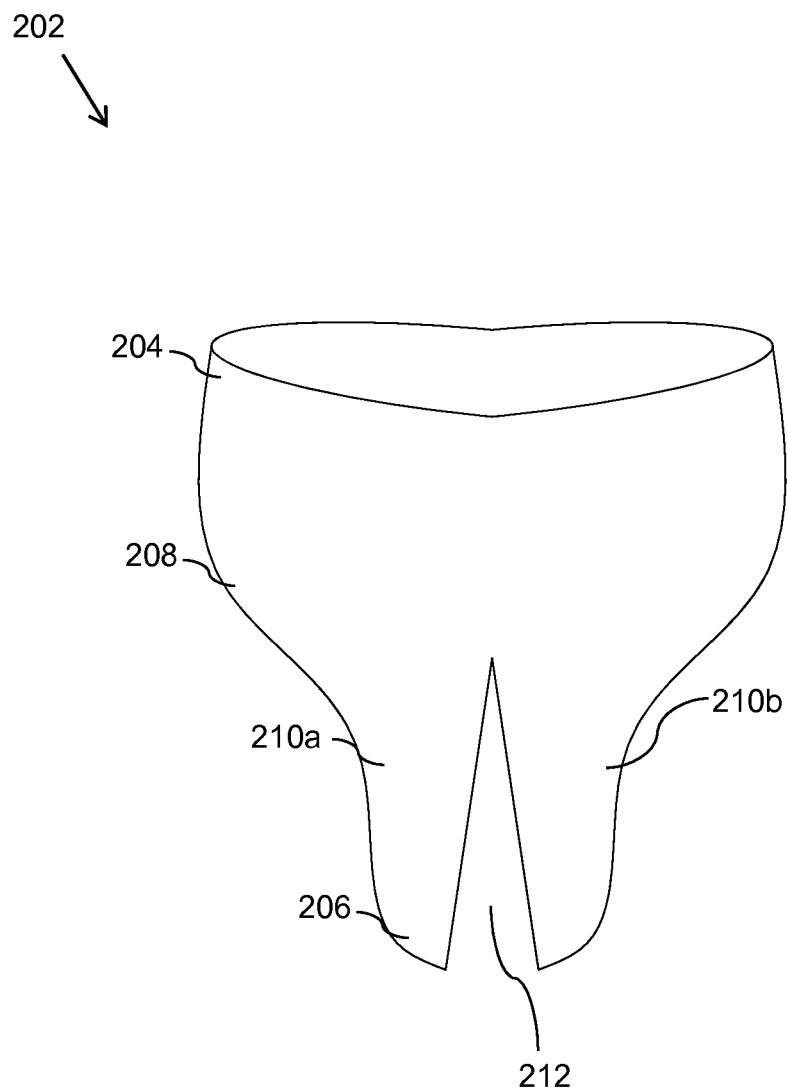

FIG. 2B is a perspective illustration of the valve member 202 in an opened configuration. The opened configuration is achieved when the first flap 210*a* and the second flap 210*b* are at a second position. As illustrated, the first flap 210*a* and the second flap 210*b* that define a planar configuration toward the bottom portion 206 detaches from one another for opening the valve member 202. The opened configuration of the first and the second flaps 210*a* and 210*b* allows flow of the bodily material from the bodily passageway. A slit or an opening 212 is formed when the valve member 202 is in the opened configuration. The slit 212 acts as an outlet orifice for relieving the bodily material outside the bodily passageway. The size of the slit 212 depends on the extent of gap between the first flap 210*a* and the second flap 210*b* after they have reached the second position. This gap can be adjusted or set depending on the intended use, and the nature and severity of the disease to be treated.

Figure 3A:
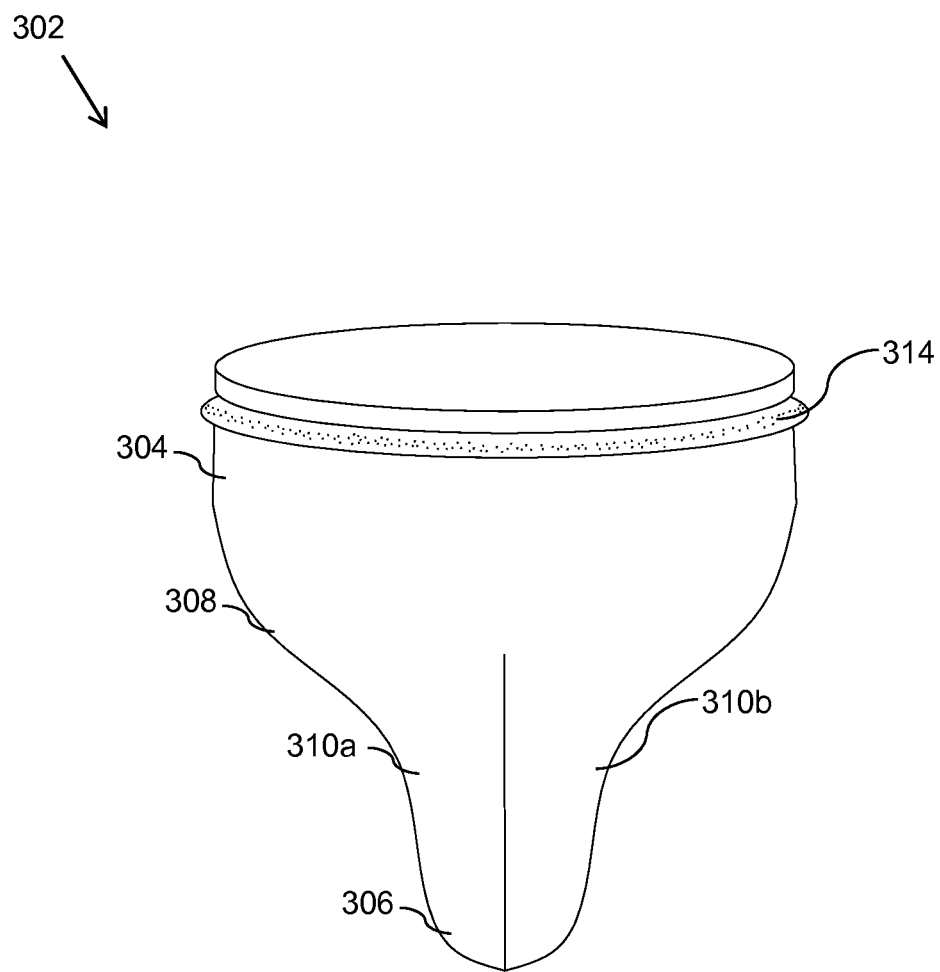
FIGS. 3A and 3B illustrate perspective views of a valve member in closed and opened configurations, respectively, in accordance with another embodiment of the present invention.

FIG. 3A is a perspective illustration of a valve member 302 in a closed configuration, in accordance with another embodiment.

As illustrated in FIG. 3A, the valve member 302 includes an upper portion 304, a bottom portion 306, and a body portion (medial portion) 308 similar to the valve member 102 and 202. The upper portion 304 of the valve member 302 forms an inlet port for a bodily material flowing through the bodily passageway and the bottom portion 306 of the valve member 302 forms an outlet port for the bodily material flowing through the bodily passageway. The valve member 302 further includes a raised portion or shoulder or lip 314 provided on its upper portion 304. The raised portion 314 facilitates engagement of a securing member such as the securing member 104 with the valve member 302. The raised portion 314 can be designed in the form of an extended surface such as a protruding surface. In some embodiments, the raised portion 314 secures the securing member, such as the securing member 104, by exerting more holding force in addition to the operating frictional force. This avoids slipping of the securing member 104 from its intended location on the valve member 302, especially when the bodily passageway is filled with the bodily material. Therefore, correct position and placement of the valve member 302 may be ensured by fixing the securing member 104 with the raised portion 314.

In accordance with some embodiments, the securing member such as the securing member 104 is positioned below the raised portion 314 such that owing to the developed pressure that pushes the valve member 302 downward, the raised portion 314 produces an upward retaining force to retain the valve member 302 in place. In some embodiments, as illustrated in FIG. 3A, the raised portion 314 is provided around the valve member 302 to form a complete loop. In some other embodiments, the raised portion 314 may be provided on some portion or at distinct locations circumferentially without forming a complete loop.

In accordance with various embodiments, width and height of the raised portion 314 may vary depending on the dimensions of the securing member, such as the securing member 104 and the valve member 302, and the predetermined pressure developed within the bodily passageway. For example, the more the developed predetermined pressure, the more upward retaining force is required to hold the valve member 302 in place. According to some embodiments, the raised portion 314 is integrally formed with the valve member 302. In some embodiments, the material of the valve member 302 and the raised portion 314 is the same. In some other embodiments, the material of the valve member 302 and the material of the raised portion 314 are different. In accordance with various embodiments, the raised portion 314 may have various shapes such as circular, conical, rectangular, and the like.

As illustrated in FIG. 3A, the valve member 302 includes two flaps (a first flap 310*a* and a second flap 310*b*) that are configured to contact one another when the two flaps 310*a* and 310*b* are at a first position similar to the flaps described in conjunction with FIG. 2A. The first position of the first and the second flaps 310*a* and 310*b* defines the closed configuration such that the flow of a bodily material is restricted in this condition. In embodiments, the design of the flaps 310*a* and 310*b* can be similar to the design of the flaps described in conjunction with FIGS. 1 and 2.

Figure 3B:
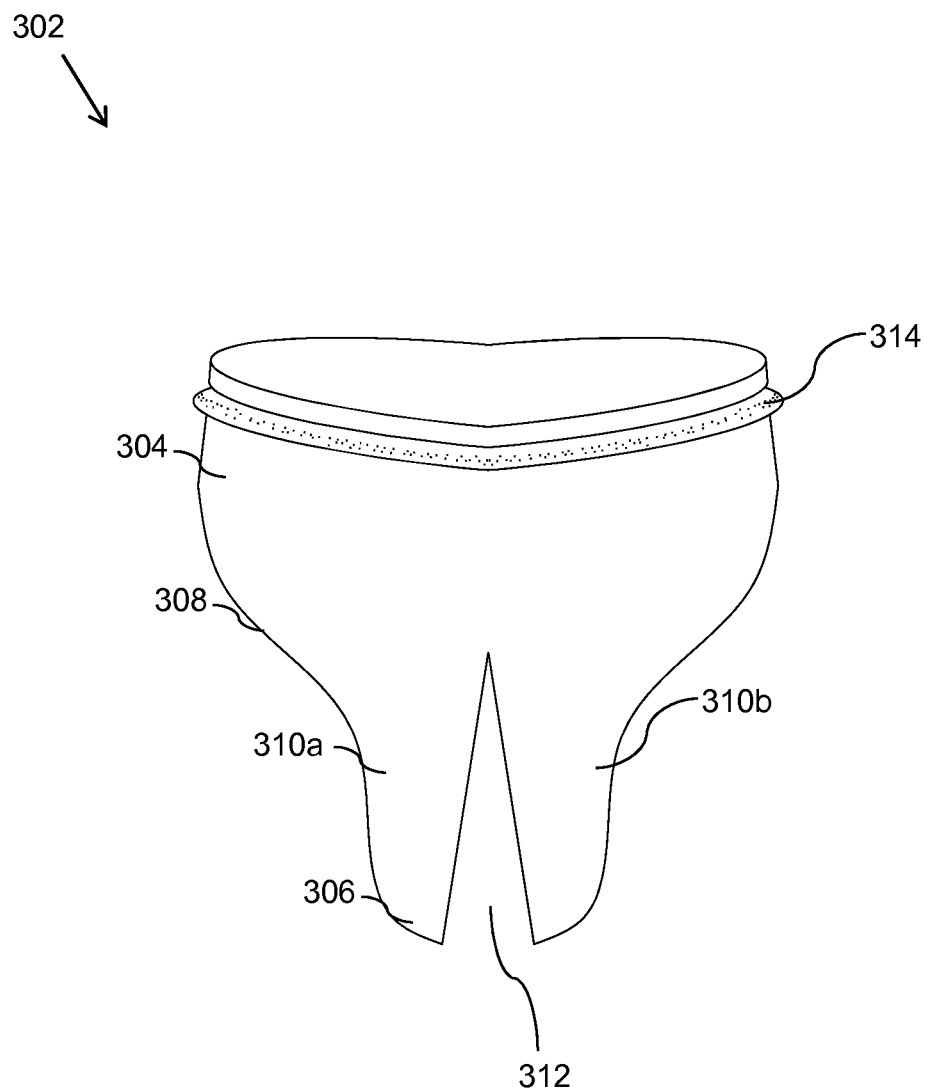

FIG. 3B is a perspective illustration of the valve member 302 in an opened configuration. The opened configuration is achieved when the first flap 310*a* and the second flap 310*b* are at a second position. The opening mechanism of the valve member 302 (to achieve the opened configuration) is similar to that described in conjunction with FIGS. 1 and 2. The opened configuration of the first and the second flaps 310*a* and 310*b* allows flow of the bodily material from the bodily passageway. A slit or an opening 312 similar to the slit 212 is formed when the valve member 302 is in the opened configuration. The slit 312 acts as an outlet orifice for relieving the bodily material outside the bodily passageway.

Figure 4A:
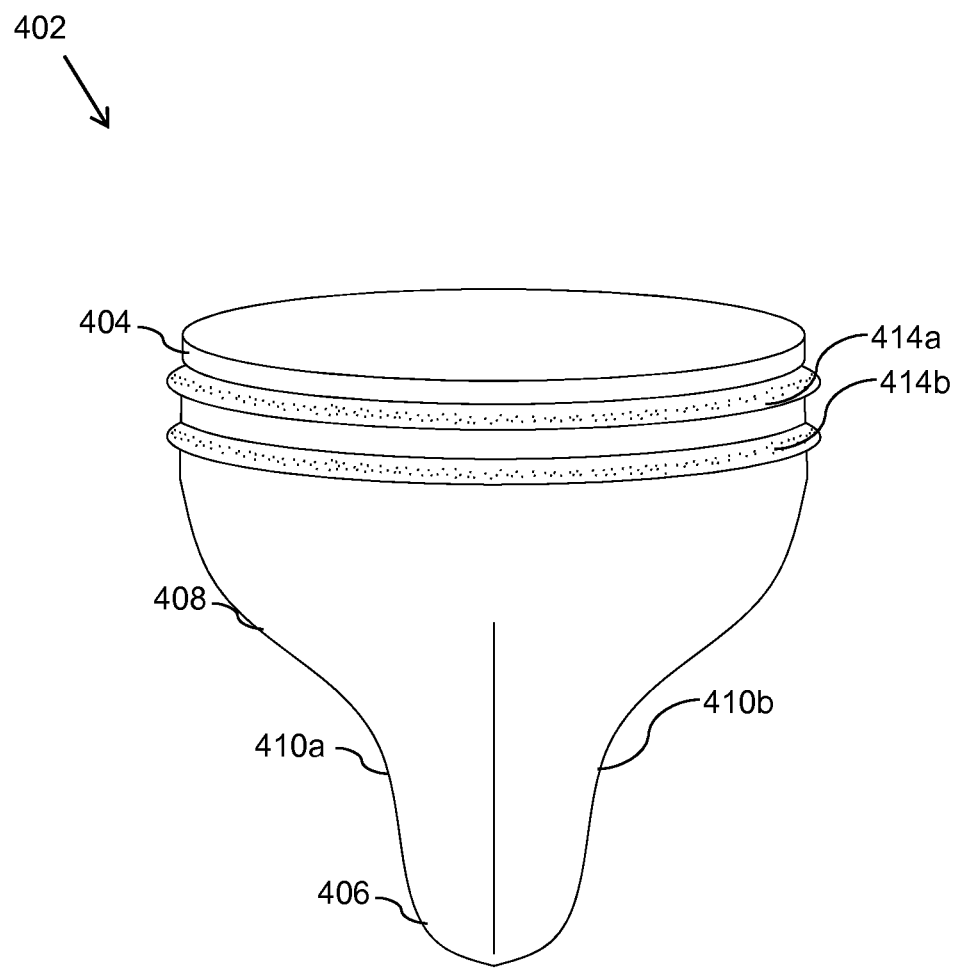
FIGS. 4A and 4B illustrate perspective views of a valve member in closed and opened configurations, respectively, in accordance with another embodiment of the present invention.

FIG. 4A is a perspective illustration of a valve member 402 in a closed configuration, in accordance with another embodiment.

As illustrated in FIG. 4A, the valve member 402 includes an upper portion 404, a bottom portion 406, and a body portion (medial portion) 408 similar to the valve member 102, 202, and 302. The upper portion 404 of the valve member 402 forms an inlet port for a bodily material flowing through the bodily passageway and the bottom portion 406 of the valve member 402 forms an outlet port for the bodily material flowing through the bodily passageway. The valve member 402 further includes a first raised portion 414*a* and a second raised portion 414*b* provided on its upper portion 404. The first raised portion 414*a* and the second raised portion 414*b* facilitate engagement of a securing member, such as the securing member 104, with the valve member 402. The first raised portion 414*a* and the second raised portion 414*b* (hereafter referred to as raised portions 414*a* and 414*b* together for simplicity of the description) can be designed in the form of an extended surface such as a protruding surface.

In some embodiments, the raised portions 414*a* and 414*b* secure the securing member, such as the securing member 104, by exerting more holding force in addition to the operating frictional force. The holding force is capable of retaining the valve member in place. Further, the securing member 104 is configured to be properly fitted and engaged between the first raised portion 414a and the second raised portion 414b. This avoids slipping of the securing member such as the securing member 104 from its intended location on the valve member 402, especially when the bodily passageway is completely filled with the bodily material. A correct position and placement of the valve member 402 may be ensured by fitting the securing member, such as the securing member 104, between the raised portions 414a and 414b.

In accordance with some embodiments, the securing member, such as the securing member 104, is positioned between the first raised portion 414a and the second raised portion 414b such that owing to the developed pressure that pushes the valve member 402 downward, the raised portions 414a and 414b keeps engaging the securing member such as the securing member 104, thereby retaining the valve member 402 in place. In some embodiments, as illustrated in FIG. 4A, the raised portions 414a and 414b are provided to form a complete loop around the valve member 402. In some other embodiments, the raised portions 414a and 414b may be provided on some portions or at distinct locations circumferentially without forming a complete loop.

In accordance with various embodiments, the dimensions, materials, designs, and profiles of the raised portions 414a and 414b may vary similar to the dimensions, materials, designs, and profiles of the raised portion 314 described in conjunction with FIG. 3. In some embodiments, the dimension, design, and profile of the first raised portion 414a are similar to the dimension, design, and profile of the second raised portion 414b. In some other embodiments, the dimension, design, and profile of the first raised portion 414a are different than the dimension, design, and profile of the second raised portion 414b. Further, in some embodiments, the material of the first raised portion 414a is similar to the material of the second raised portion 414b. In certain other embodiments, the material of the first raised portion 414a is different than the material of the second raised portion 414b.

As illustrated, the valve member 402 includes two flaps (a first flap 410a and a second flap 410b) that are configured to contact one another when the two flaps 410a and 410b are at a first position similar to the flaps described in conjunction with FIGS. 2A and 3A. The first position of the first and the second flaps 410a and 410b defines the closed configuration such that the flow of a bodily material is restricted in this condition. The design and profile of the flaps 410a and 410b can be similar to the design and profile of the flaps described in conjunction with FIGS. 1 and 2.

Figure 4B:
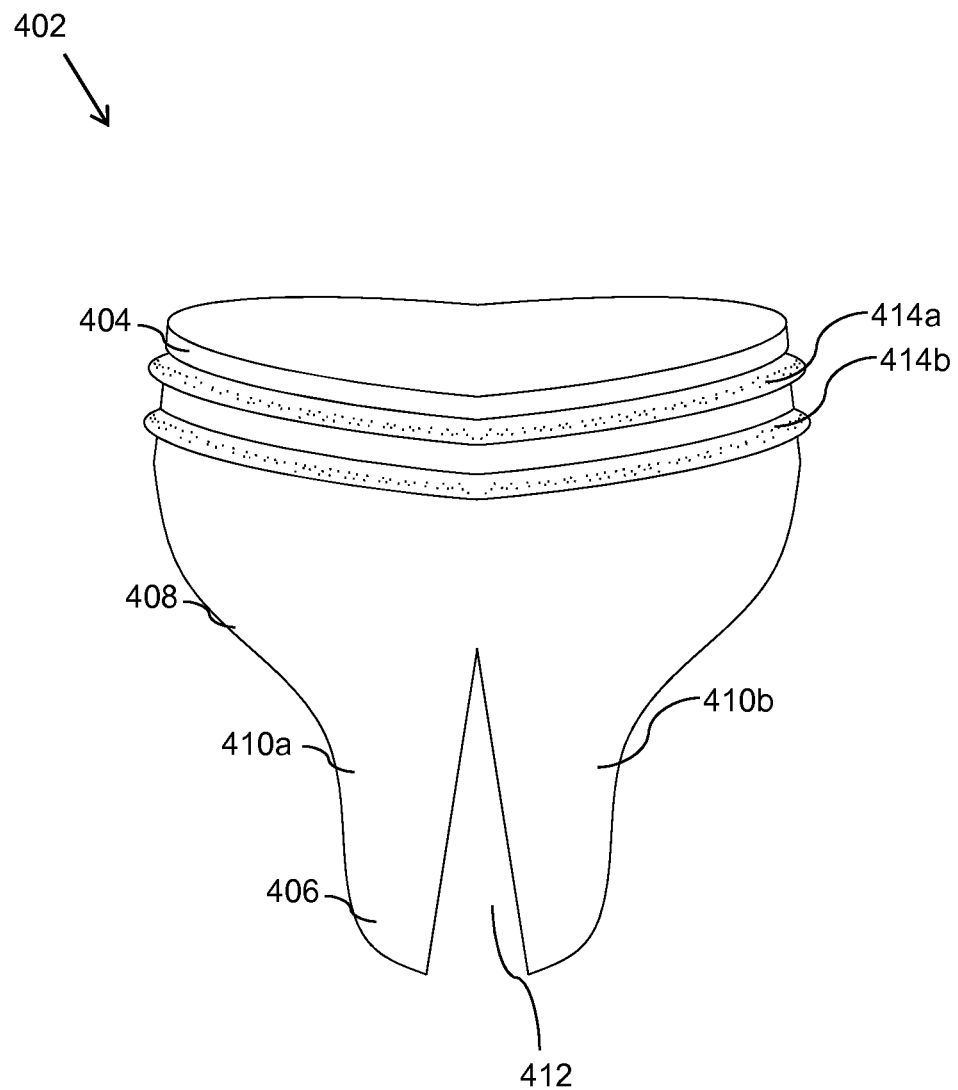

FIG. 4B is a perspective illustration of the valve member 402 in an opened configuration. The opened configuration is achieved when the first flap 410a and the second flap 410b are at a second position. The opening mechanism of the valve member 402 (to achieve the opened configuration) is similar to that described in conjunction with FIGS. 1, 2, and 3. The opened configuration of the first and the second flaps 410a and 410b allows flow of the bodily material from the bodily passageway. A slit or an opening 412 similar to the slit 212 or 312 is formed when the valve member 402 is in the opened configuration.

Figure 5A:
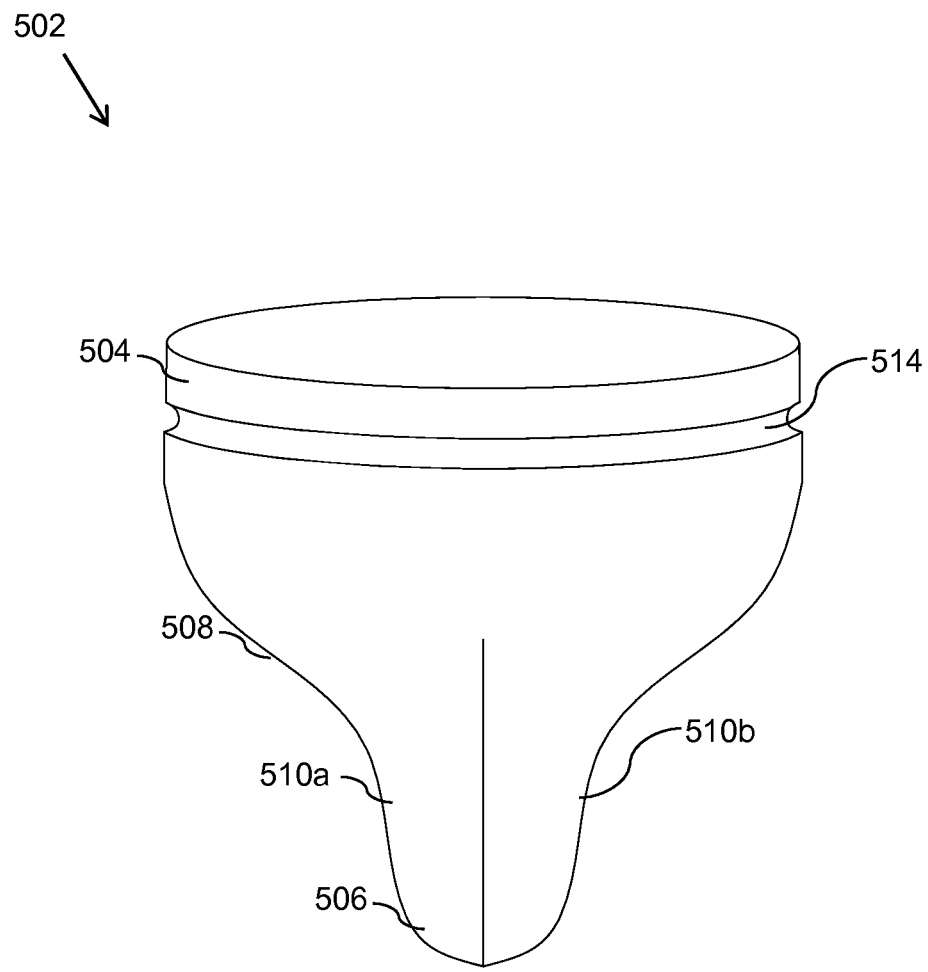
FIGS. 5A and 5B illustrate perspective views of a valve member in closed and opened configurations, respectively, in accordance with another embodiment of the present invention.

FIG. 5A is a perspective illustration of a valve member 502 in a closed configuration, in accordance with another embodiment.

As illustrated, the valve member 502 includes an upper portion 504, a bottom portion 506, and a body portion (medial portion) 508 similar to the valve member 102, 202, 302, and 402. The upper portion 504 of the valve member 502 forms an inlet port for a bodily material flowing through the bodily passageway and the bottom portion 506 of the valve member 502 forms an outlet port for the bodily material flowing through the bodily passageway. The valve member 502 further includes a groove 514 provided on its upper portion 504. The groove 514 facilitates engagement of a securing member such as the securing member 104 with the valve member 502. In some embodiments, the groove 514 secures the securing member, such as the securing member 104, by exerting more holding force in addition to the operating frictional force. Further, the securing member, such as the securing member 104, is configured to be properly fitted and engaged within the concave hollow curvature of the groove 514. This avoids slipping of the securing member, such as the securing member 104, from its intended location on the valve member 502, especially when the bodily passageway is filled with the bodily material. A correct position and placement of the valve member 502 may thus be ensured by fitting the securing member, such as the securing member 104, within the groove 514.

In accordance with various embodiments, the groove 514 may include various dimensions, design, and profile based on the requirements.

As illustrated, the valve member 502 includes two flaps (a first flap 510a and a second flap 510b) that are configured to contact one another when the two flaps 510a and 510b are at a first position similar to the flaps described in conjunction with FIGS. 2A and 3A, and 4A. The first position of the first and the second flaps 510a and 510b defines the closed configuration such that the flow of a bodily material is restricted in this condition. The design and profile of the flaps 510a and 510b can be similar to the design and profile of the flaps described in conjunction with FIGS. 1 and 2.

Figure 5B:
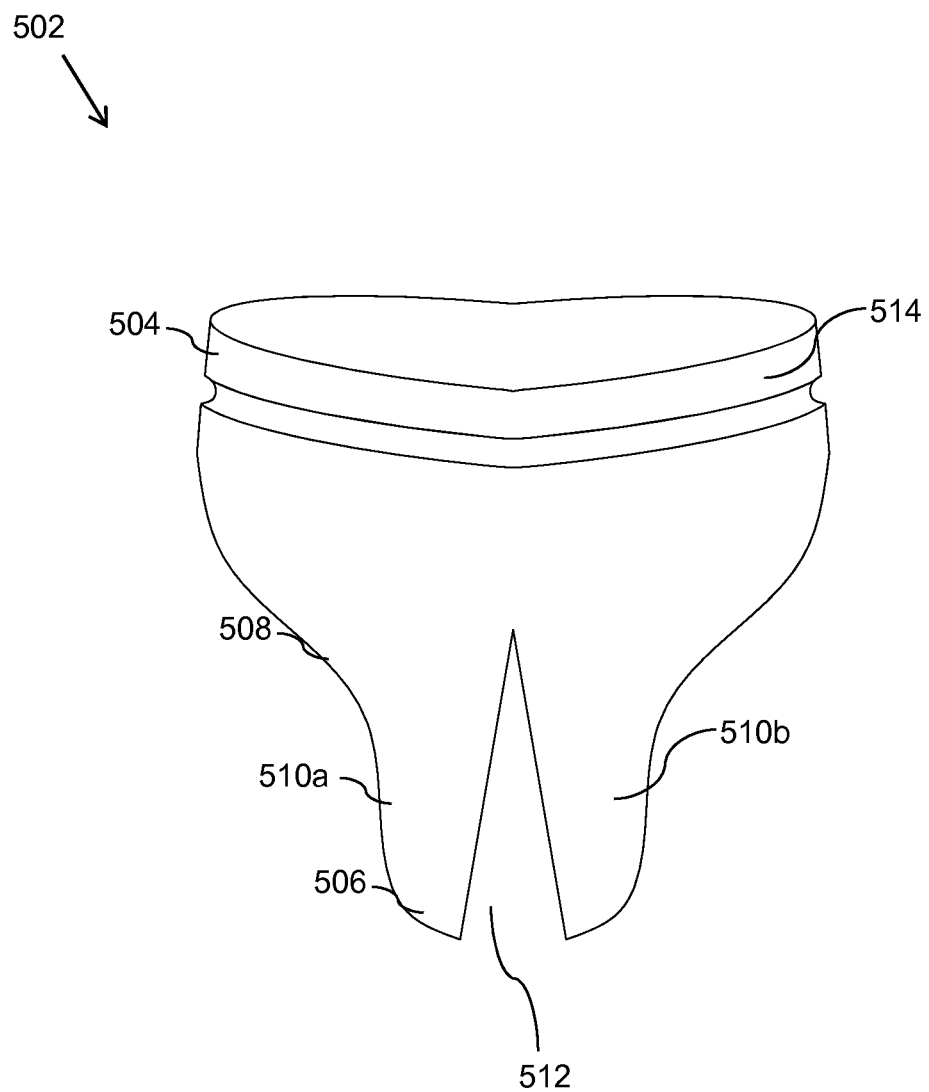

FIG. 5B is a perspective illustration of the valve member 502 in an opened configuration. The opened configuration is achieved when the first flap 510a and the second flap 510b are at a second position. The opening mechanism of the valve member 502 (to achieve the opened configuration) is similar to that described in conjunction with FIGS. 1, 2B, 3B, and 4B. The opened configuration of the first and the second flaps 510a and 510b allows flow of the bodily material from the bodily passageway. A slit or an opening 512 similar to the slit 212 or 312 or 412 is formed when the valve member 502 is in the opened configuration.

Some types of engaging mechanism or structures such as a raised portion, a set of first and second raised portions, and a groove have been described in conjunction with various figures above. However, several other types of structures and mechanisms in addition to those disclosed above can be utilized for engaging the securing member with the valve member to retain it in place. For example, in some embodiments, hooks or protruded spots/locations may be utilized.

Figure 6A:
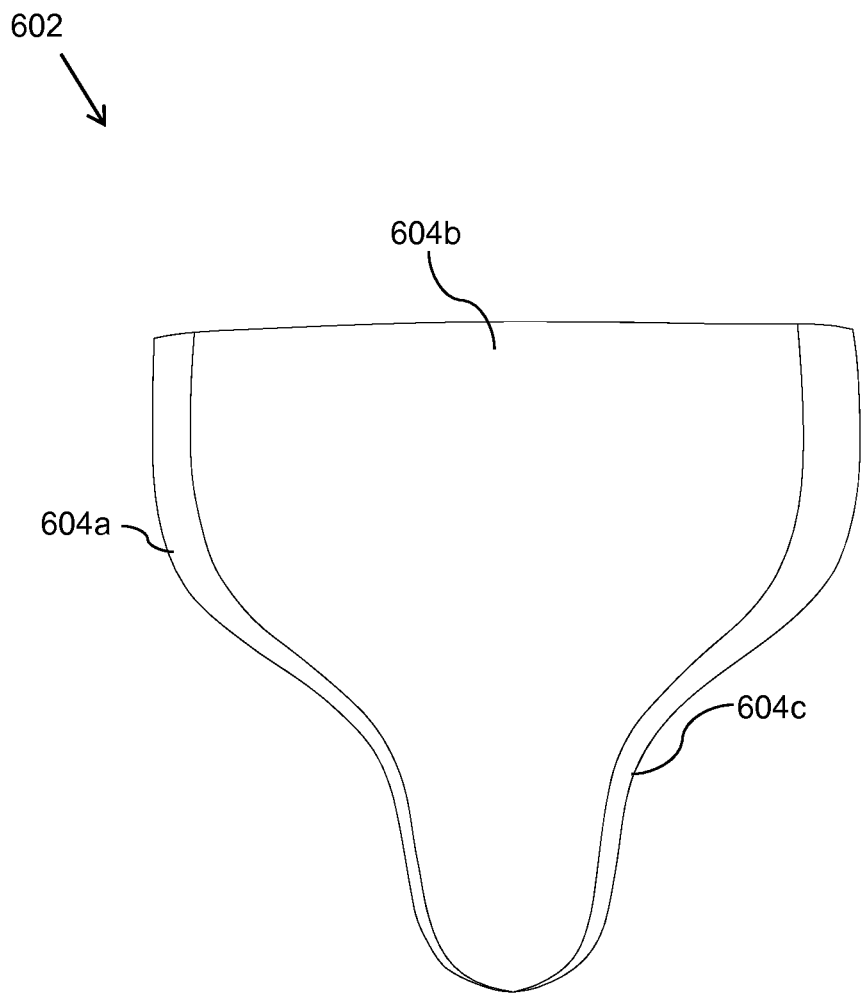
FIGS. 6A and 6B illustrate perspective views of a valve member in closed and opened configurations, respectively, in accordance with another embodiment of the present invention.
Figure 6B:
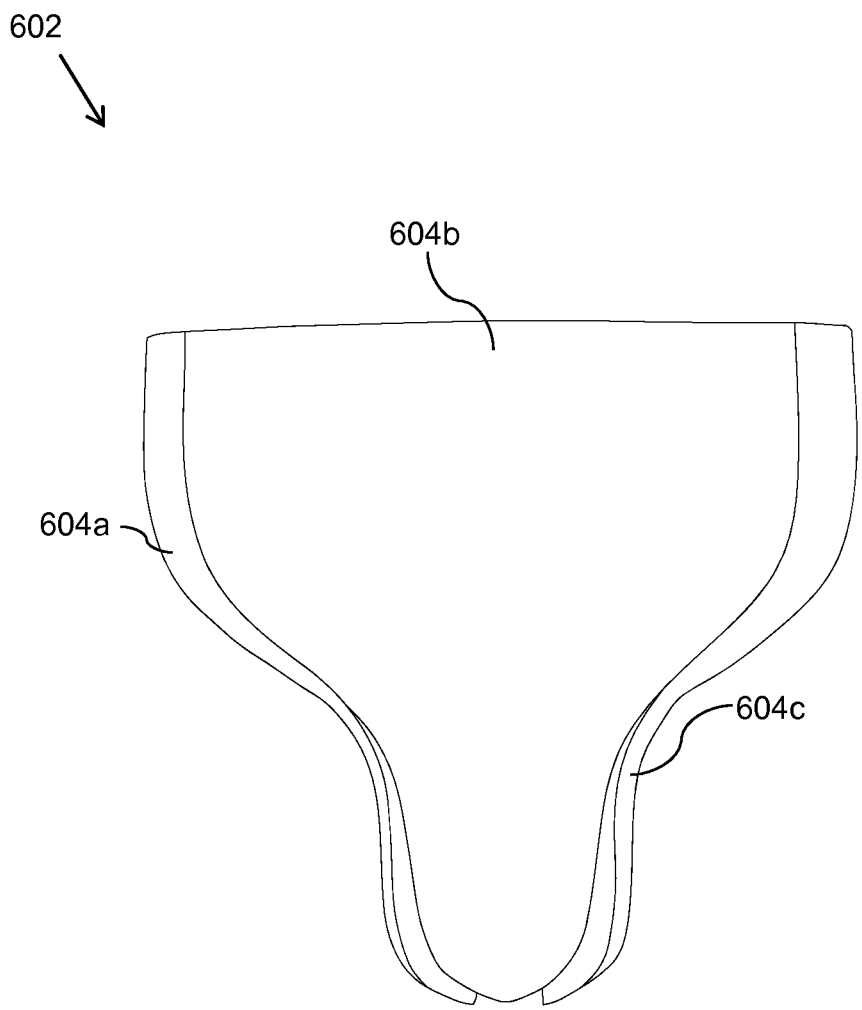

The valve member described above in conjunction with FIGS. 2-5B include two flaps. It must be appreciated that the valve member can include more than two flaps in accordance with some other embodiments. For example, in some embodiments, the valve member such as the valve member 602 can include three flaps—a first flap 604a, a second flap 604b, and a third flap 604c—as shown in FIGS. 6A and 6B. FIG. 6A is a perspective illustration of the valve member 602 in a closed configuration and FIG. 6B is a perspective illustration of the valve member 602 in an opened configuration.

Figure 7:
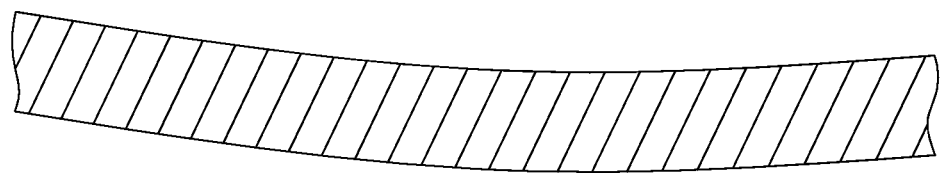
FIG. 7 is a perspective illustration of a securing member, in accordance with an embodiment.

FIG. 7 is a perspective illustration of a securing member 700, in accordance with an embodiment. The securing member 700 is configured to be positioned outside a bodily passageway such as a urethra, an anal canal, or a rectum of a patient. As illustrated, the securing member 700 can be an elastomeric band configured to be stretched to a desired length and tied or secured around a bodily passageway. The securing member 700 is configured to generate a sufficient holding force, for example, due to friction, and help retain a valve member such as the valve member 102, 202, 302, 402, 502, and 602 in place within the bodily passageway. Some examples of elastomers that can be utilized in manufacturing the securing member 600 are discussed in conjunction with FIG. 1.

Figure 8:
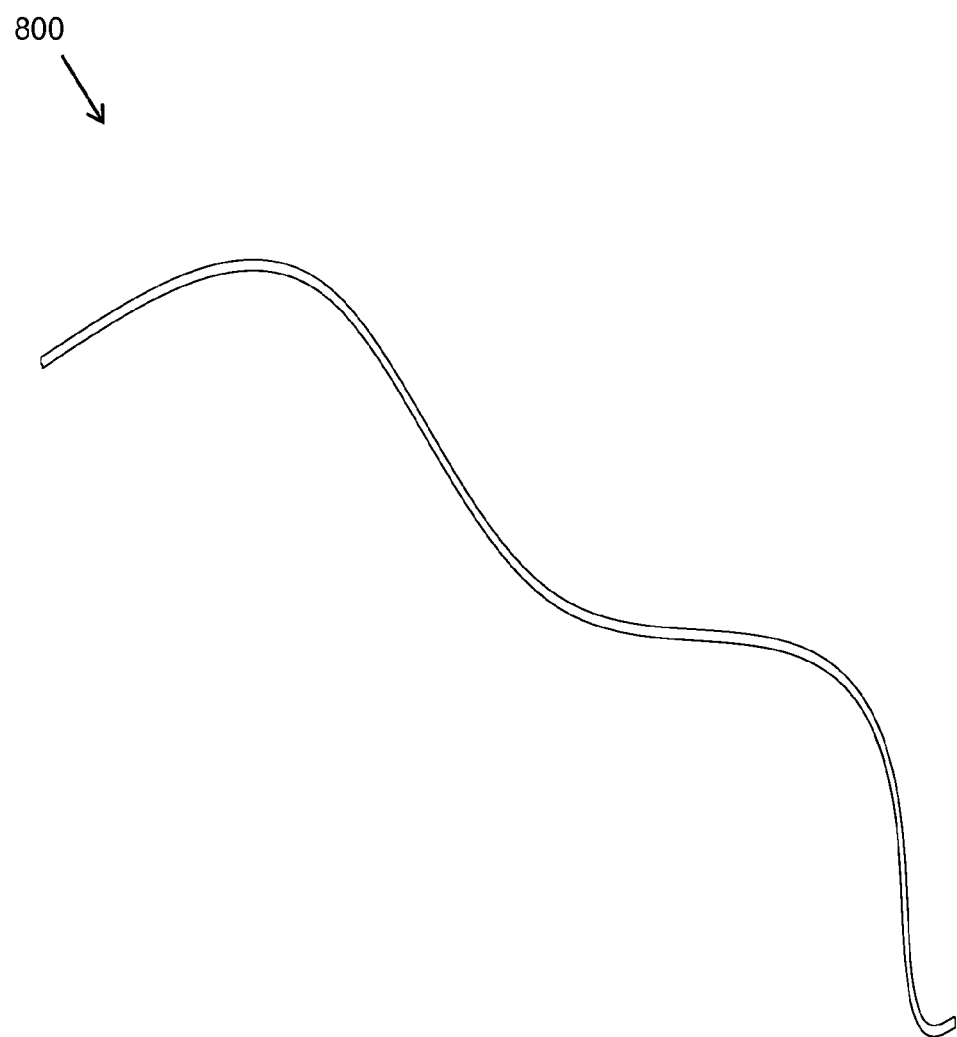
FIG. 8 is a perspective illustration of a securing member, in accordance with another embodiment.

FIG. 8 is a perspective illustration of a securing member 800, in accordance with another embodiment. As illustrated, the securing member 800 can be any kind of a suture. In some embodiments, the securing member 800 (in the form of a suture) can be made from both natural and synthetic materials. The securing member 800 can include a monofilament structure or a multifilament structure. Several types of polymers and elastomeric materials may be utilized in the securing member 800. A few examples of such materials have been described in conjunction with FIG. 1.

Figure 9A:
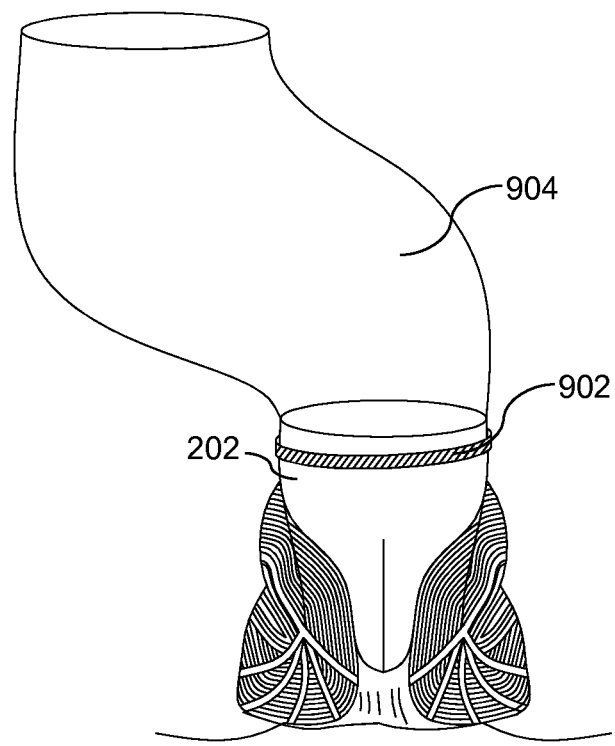
FIGS. 9A and 9B illustrate perspective views of placement of a medical device, in accordance with an embodiment of the present invention.
Figure 9B:
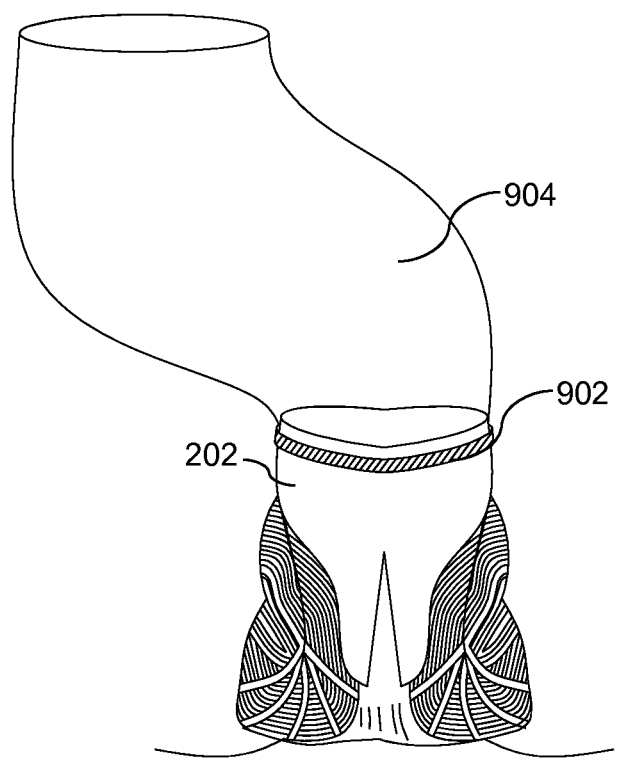

FIGS. 9A and 9B depict perspective views of placement of a medical device in accordance with an embodiment of the present invention. The medical device includes the valve member 202 as described in conjunction with FIGS. 2A and 2B, and a securing member 902. As shown, the valve member 202 is positioned inside the bodily passageway 904 and the securing member 902 is positioned outside the bodily passageway 904. In some embodiments, the securing member 902 is configured to help retain the valve member within the bodily passageway 904 via friction. FIG. 9A shows a closed configuration and FIG. 9B shows an opened configuration of the valve member 202.

Figure 10A:
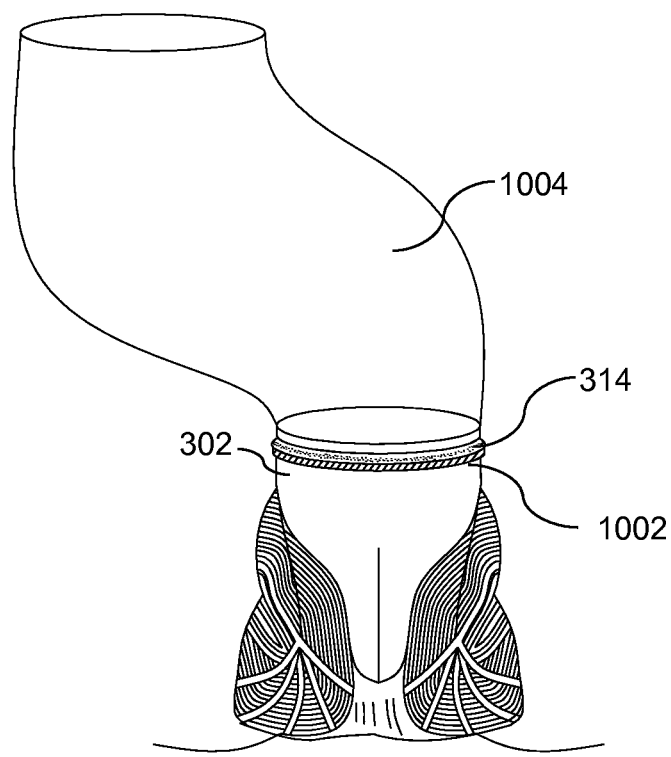
FIGS. 10A and 10B illustrate perspective views of placement of a medical device, in accordance with another embodiment of the present invention.
Figure 10B:
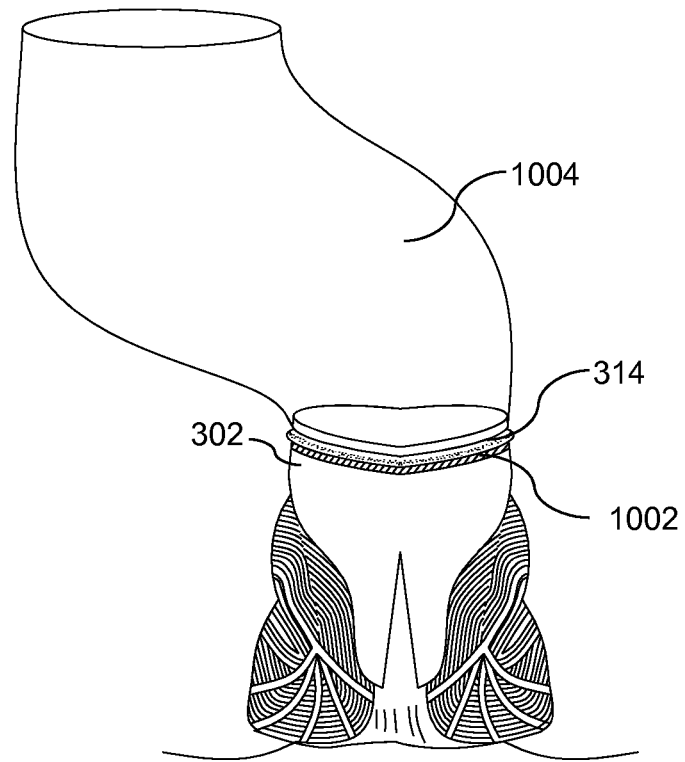

FIGS. 10A and 10B depict perspective views of placement of a medical device in accordance with another embodiment of the present invention. The medical device includes the valve member 302 as described in conjunction with FIGS. 3A and 3B, and a securing member 1002. The valve member 302 further includes the raised portion 314. As shown, the valve member 302 is positioned inside a bodily passageway 1004 and the securing member 1002 is positioned outside the bodily passageway 1004. In some embodiments, the securing member 1002 is configured to help retain the valve member within the bodily passageway 1004 via friction and via abutment or engagement with the raised portion 314. FIG. 10A shows a closed configuration and FIG. 10B shows an opened configuration of the valve member 302.

Figure 11A:
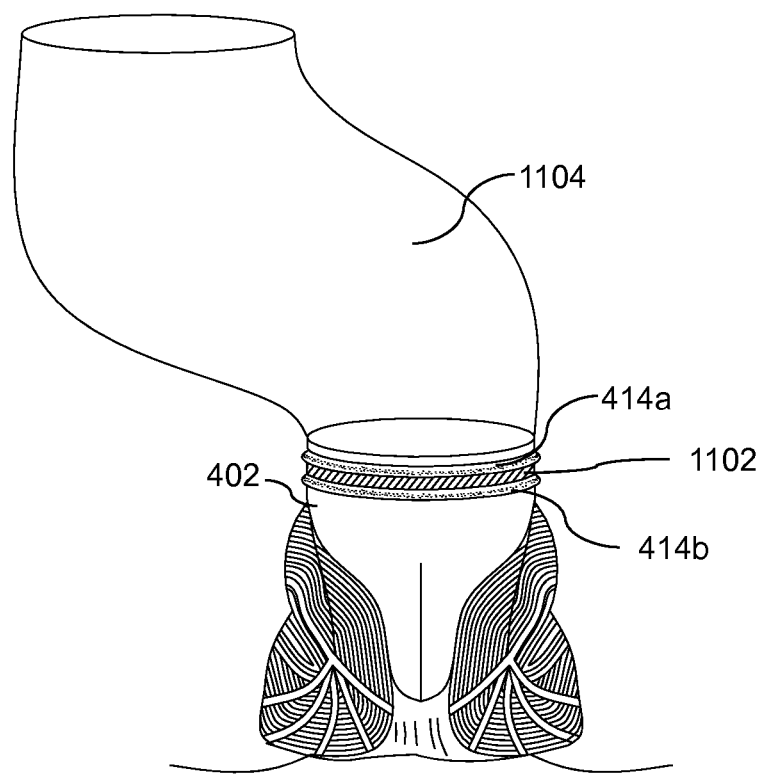
FIGS. 11A and 11B illustrate perspective views of placement of a medical device, in accordance with another embodiment of the present invention.
Figure 11B:
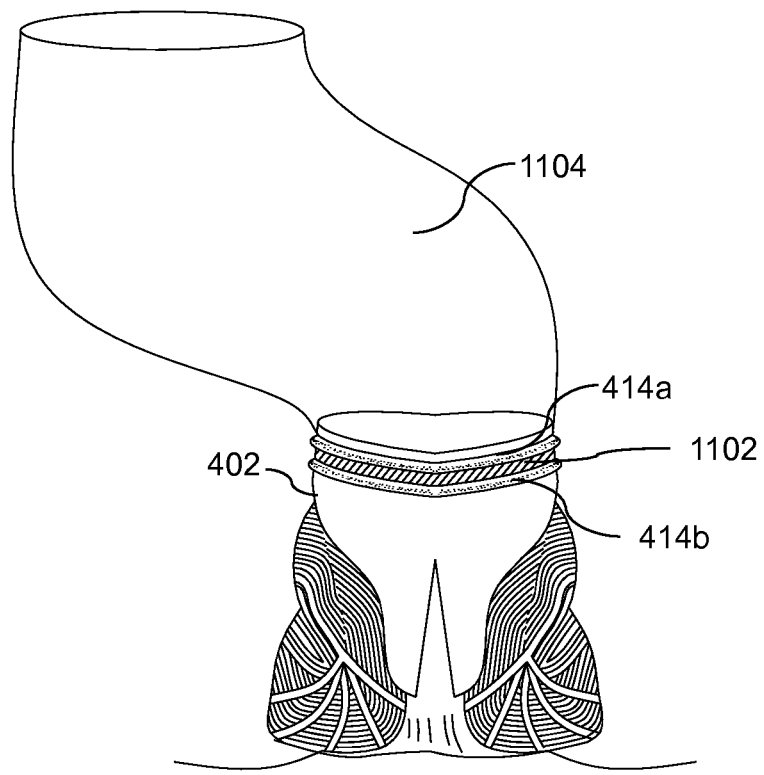

FIGS. 11A and 11B depict perspective views of placement of a medical device in accordance with another embodiment of the present invention. The medical device includes the valve member 402 as described in conjunction with FIGS. 4A and 4B, and a securing member 1102. The valve member 402 further includes the first raised portion 414a and the second raised portion 414b. As shown, the valve member 402 is positioned inside a bodily passageway 1104 and the securing member 1102 is positioned outside the bodily passageway 1104 between the first raised portion 414a and the second raised portion 414b. In some embodiments, the securing member 1102 is configured to help retain the valve member within the bodily passageway 1104 via friction and via abutment or engagement with the raised portions 414a and 414b. FIG. 11A shows a closed configuration and FIG. 11B shows an opened configuration of the valve member 402.

Figure 12A:
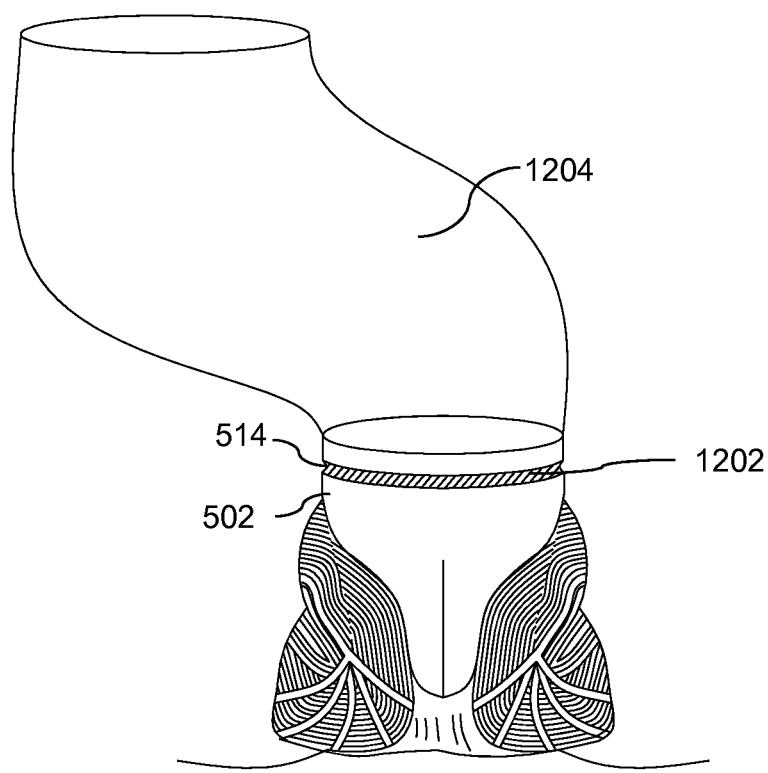
FIGS. 12A and 12B illustrate perspective views of placement of a medical device, in accordance with another embodiment of the present invention.
Figure 12B:
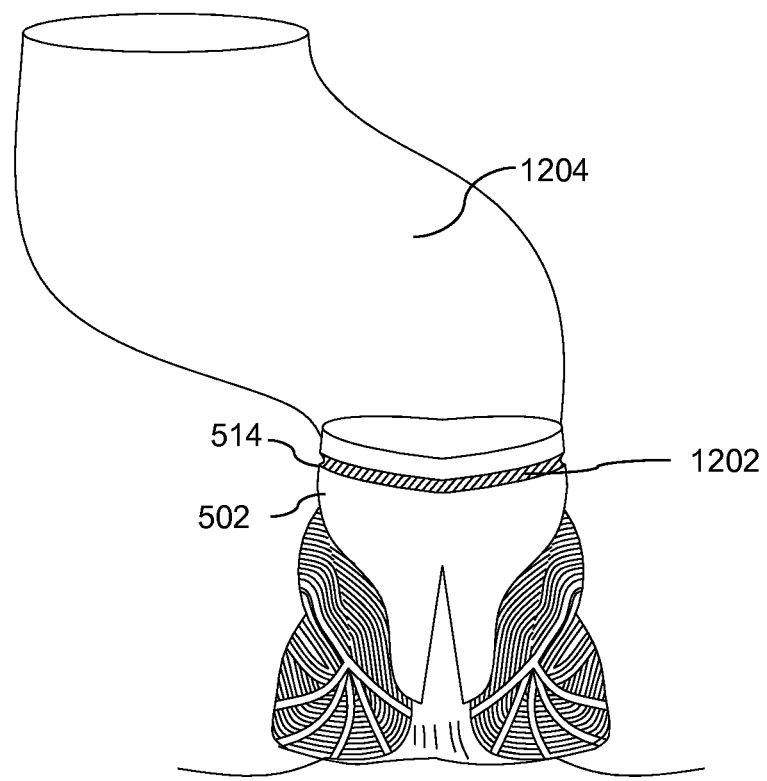

FIGS. 12A and 12B depict perspective views of placement of a medical device in accordance with another embodiment of the present invention. The medical device includes the valve member 502, as described in conjunction with FIGS. 5A and 5B, and a securing member 1202. The valve member 502 further includes the groove 514 on the upper portion. As shown, the valve member 502 is positioned inside a bodily passageway 1204 and the securing member 1202 is positioned outside the bodily passageway 1204. The securing member 1202 engages within the concave hollow space provided by the groove 514. In some embodiments, the securing member 1202 is configured to help retain the valve member within the bodily passageway 1204 via friction and via abutment or engagement with the groove 514. FIG. 12A shows a closed configuration and FIG. 12B shows an opened configuration of the valve member 502.

Figure 13:
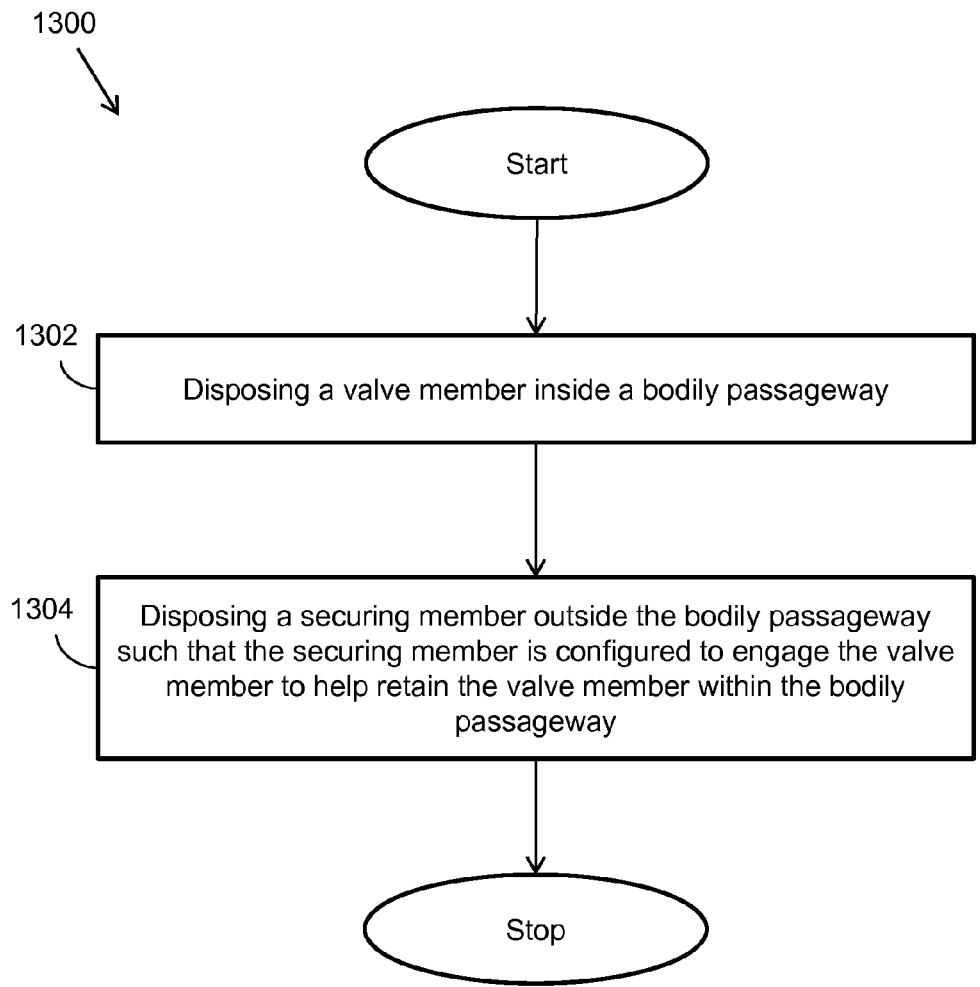
FIG. 13 is a flowchart illustrating a method of placement of a medical device, in accordance with an embodiment of the present invention.

FIG. 13 is a flowchart illustrating a method of placement of the medical device in accordance with various embodiments. Referring now to FIG. 13 in conjunction with FIGS. 9A-12B, the method of placement of the medical device is described. The medical device includes a valve member such as the valve member 102 and a securing member such as the securing member 104. As illustrated in FIG. 13, the method includes disposing the valve member 102 inside a bodily passageway at step 1302. In some embodiments, an operator may advance the valve member 102 up the anal canal in order to dispose it inside the bodily passageway 1302. In accordance with the illustrated embodiments, an anal canal is depicted in FIGS. 9A-13B. However, the medical device can be disposed in other bodily passageways such as a urethra of a patient. In accordance with several embodiments, the valve member 102 can be of any type such as those described in conjunction with FIGS. 1, and 2A-5B. It must be appreciated that the method steps are described with reference to the valve member 102 and the securing member 104 merely for simplicity of the description. However, in accordance with various other embodiments, several other types of valves members such as the valve member 202, 302, 402, 502, and 602 may be employed. Similarly, several other types of securing members such as the securing member 204, 304, 404, and 504 may be employed.

The method further includes disposing the securing member 104 outside the bodily passageway at step 1304, such that the securing member 104 is configured to engage the valve member 102 to help retain the valve member 102 within the bodily passageway.

In accordance with some embodiments, the securing member 104 can be placed from an inner wall of the bodily passageway (anal canal in this case). The operator inserts a delivery tool through the anal canal to reach inside the bodily passageway. Thereafter, an opening is made in an internal wall of the anal canal. The securing member is brought outside the bodily passageway through the opening to place it outside the bodily passageway circumferentially. The securing member 104 can then be tied to form a circular loop or ring outside the anal canal. Subsequently, the opening in the wall can be sutured after placing the securing member 104.

In accordance with some other embodiments, an operator can make bodily incisions in perineum, or anteriolateral, posteriolateral or lateral locations with respect to the anus of the patient. In this case, the operator inserts the delivery tool coupled with the securing member 104 through any of the incisions. The securing member 104 is then left inside the body to surround around the bodily passageway firmly. The bodily incisions can finally be sutured.

In accordance with some embodiments, the securing member 1002 may be engaged with the raised portion 314 of the valve member 302 as described in conjunction with FIGS. 10A and 10B such that the securing member 1002 is configured to retain the valve member 302 in place within the bodily passageway. In some other embodiments, the securing member 1102 may be engaged between the first raised portion 414a and the second raised portion 414b of the valve member 402 illustrated in conjunction with FIGS. 11A and 11B such that the securing member 1102 is configured to retain the valve member 402 in place within the bodily passageway. In still other embodiments, the securing member 1202 can be engaged within a groove 514 of the valve member 502 illustrated in conjunction with FIGS. 12A and 12B such that the securing member 1202 is configured to retain the valve member 502 in place within the bodily passageway.

Figure 14:
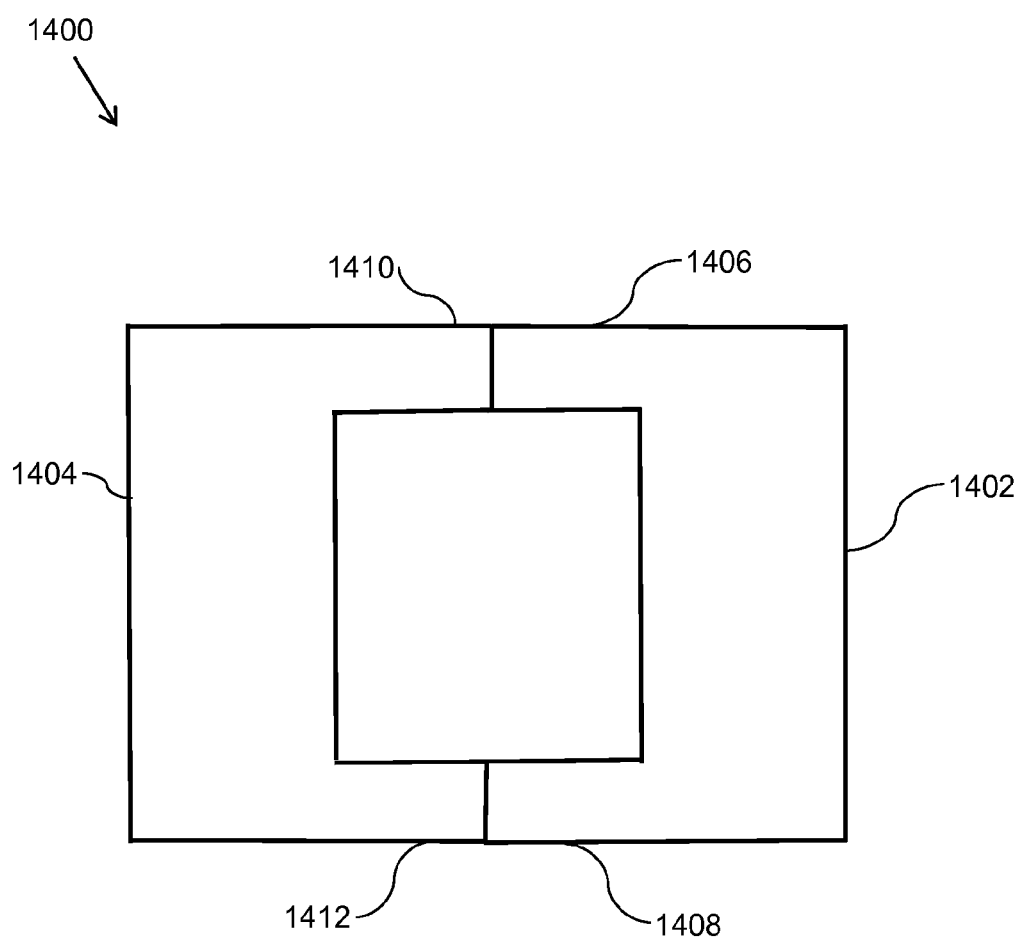
FIG. 14 is a schematic diagram of a medical device configured to be implanted within a patient's body, in accordance with an embodiment of the present invention.

FIG. 14 is a schematic diagram of a medical device 1400 configured to be implanted within a patient's body, in accordance with an embodiment of the present invention. The medical device 1400 includes a first portion 1402 and a second portion 1404, as illustrated in FIG. 14.

The first portion 1402 is configured to be placed within a body of a patient such that the first portion 1402 is disposed adjacent to a portion of a bodily passageway. In some embodiments, the first portion 1402 is disposed around the bodily passageway to surround it circumferentially. In accordance with several embodiments, the bodily passageway can be a urethra, anal canal or rectum of a patient. The first portion 1402 has a first end portion 1406 and a second portion 1408.

The second portion 1404 has a first end portion 1410 and a second end portion 1412. The first end portion 1410 of the second portion 1404 is configured to be coupled to the first end portion 1406 of the first portion 1402. The second end portion 1412 of the second portion 1404 is configured to be coupled to the second end portion 1408 of the first portion 1402. The second portion 1404 is configured to move from a first length to a second length in response to a predetermined pressure or in response to being exposed to a predetermined pressure developed within the bodily passageway. The predetermined pressure is a threshold cracking pressure that develops due to an accumulated bodily material inside the bodily passageway. In some embodiments, the accumulated bodily material can be a fecal material that accumulates inside the anal canal of a patient.

Figure 15:
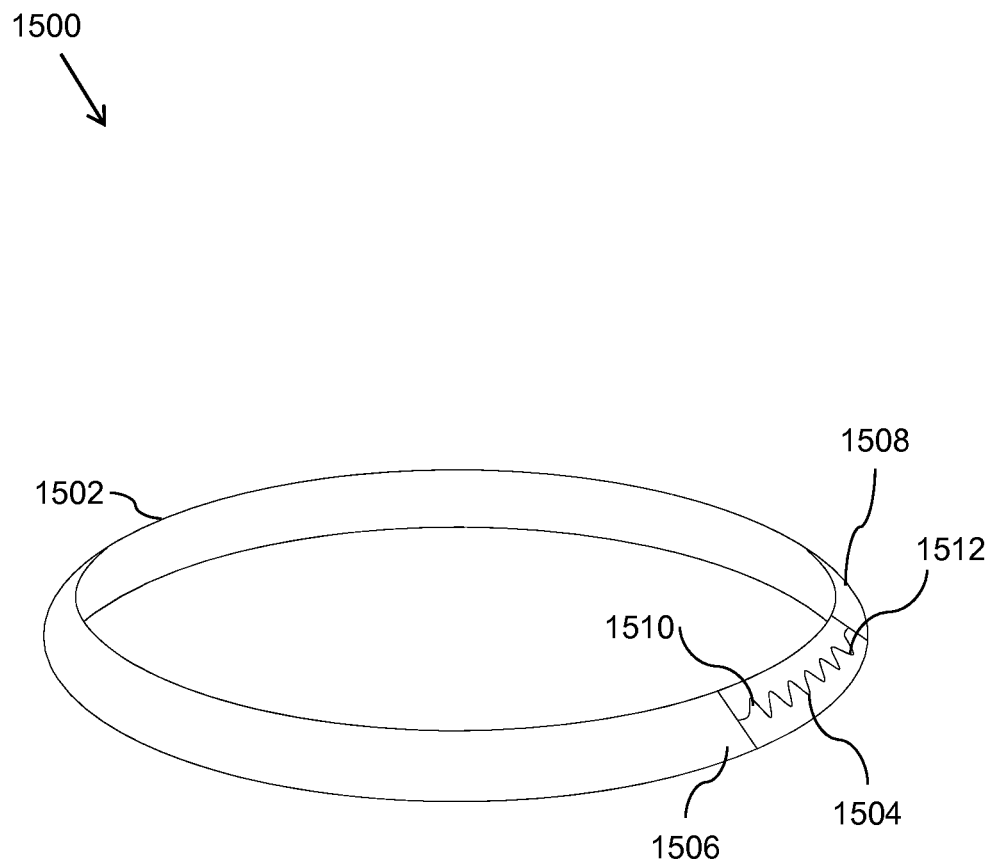
FIG. 15 is a perspective illustration of a medical device configured to be implanted within a patient's body, in accordance with an embodiment of the present invention.

FIG. 15 is a perspective illustration of a medical device 1500 configured to be implanted within a patient's body, in accordance with an embodiment. As illustrated, the medical device 1500 includes a first portion 1502 and a second portion 1504. The first portion 1502 and the second portion 1504 are shown in the coupled configuration in FIG. 15.

The first portion 1502 is configured to be placed within a body of a patient such that the first portion 1502 is disposed adjacent a portion of a bodily passageway. In some embodiments, the first portion 1502 is disposed around the bodily passageway to surround it circumferentially. In accordance with several embodiments, the bodily passageway can be a urethra, an anal canal or a rectum of a patient. The first portion 1502 has a first end portion 1506 and a second portion 1508.

The second portion 1504 has a first end portion 1510 and a second end portion 1512. The first end portion 1510 of the second portion 1504 is configured to be coupled to the first end portion 1506 of the first portion 1502. The second end portion 1512 of the second portion 1504 is configured to be coupled to the second end portion 1508 of the first portion 1502.

The second portion 1504 is configured to move from a first length to a second length in response to a predetermined pressure being developed within the bodily passageway. The predetermined pressure is a threshold cracking pressure that develops due to an accumulated bodily material inside the bodily passageway. In some embodiments, the accumulated bodily material can be a fecal material inside the anal canal of a patient.

As illustrated in FIG. 15, the second portion 1504 comprises a spring that is configured to change its length depending on the predetermined pressure. The spring is configured to change its length such that the first portion moves from a first position to a second position. At the first position, the bodily passageway is in closed configuration such that the flow of the bodily material is restricted in this condition. At the second position, the bodily passageway is in opened configuration such that the flow of the bodily material occurs in this condition. The spring constant of the spring is chosen in such a manner that the spring achieves the second length only after the predetermined pressure is achieved. This causes the bodily passageway to open and relieve the bodily material. The spring is configured to regain its shape again such that the bodily passageway gets closed after the bodily material is relieved.

In accordance with some embodiments, the second portion 1504 can include any sort of mechanism other than the spring mechanism. For example, in some embodiments, the second portion 1504 can include a piston cylinder arrangement configured to change its length from a first length to a second length by pushing the piston outward from the cylinder.

In accordance with some embodiments, the first portion 1502 is made of an elastomeric or a polymeric material. A few examples of these materials are natural polyisoprene, synthetic polyisoprene, polybutadiene, chloroprene, polychloroprene, neoprene, butyl rubber, halogenated butyl rubbers, styrene-butadiene, nitrile rubber, EPM (ethylene propylene rubber), epichlorohydrin rubber, polyacrylic rubber, silicone rubber, fluorosilicone rubber, fluoroelastomers, perfluoroelastomers, polyether block amides, chlorosulfonated polyethylene, ethylene-vinyl acetate, thermoplastic elastomers (TPE), elastin, polysulfide rubber, silicones, and the like.

In some embodiments, the second portion 1504 can be made from a metallic material. In some embodiments, the second portion can be made from Nitinol. In other embodiments, the second portion 1504 is formed of a biocompatible, shape memory material, and the like.

Figure 16:
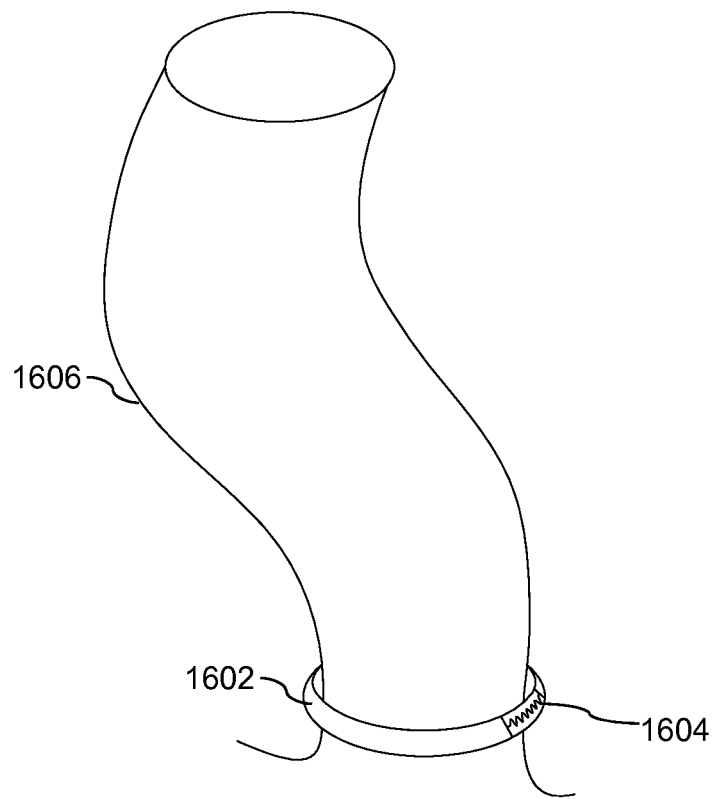
FIG. 16 is a perspective illustration of placement of a medical device, in accordance with an embodiment of the present invention.

FIG. 16 is a perspective illustration of a placement of a medical device 1600 in accordance with an embodiment of the present invention. As illustrated, the first portion 1602 is disposed adjacent to a portion of a bodily passageway 1606 (anal canal in this case) and the second portion 1604 is coupled to the first portion 1602. The bodily passageway 1606 is illustrated in the form of an anal canal in FIG. 16; however, it must be appreciated that the medical device 1600 can also be employed in other bodily passageways such as urethra.

Figure 17:
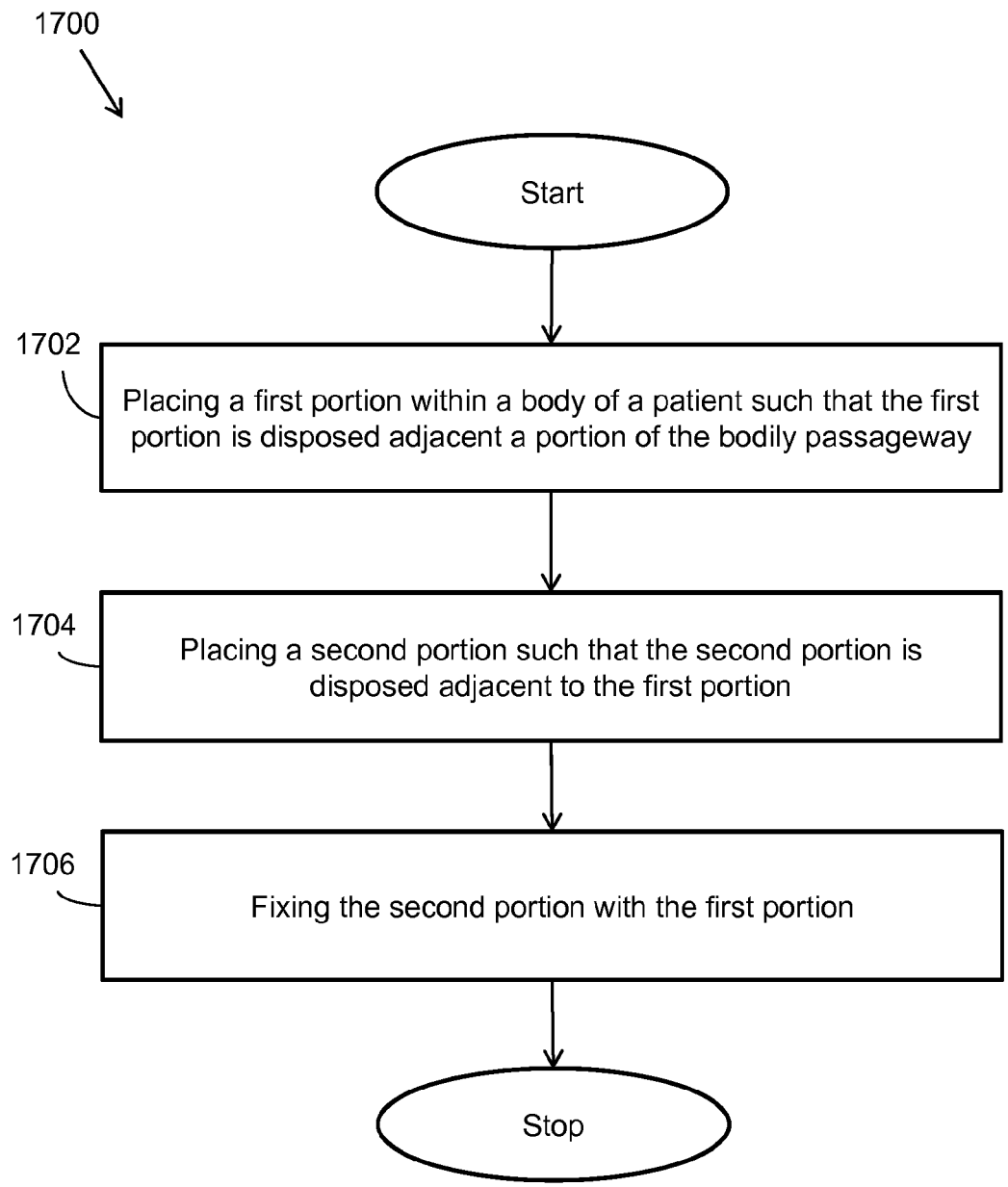
FIG. 17 is a flowchart illustrating a method of placement of a medical device, in accordance with an embodiment of the present invention.

FIG. 17 is a flowchart illustrating a method of placement of a medical device in accordance with an embodiment. In some embodiments, the medical device can be the medical device 1400 as described in conjunction with FIG. 14. In some other embodiments, the medical device can be the medical device 1500 as described in conjunction with FIG. 15.

Referring now to FIG. 17 in conjunction with FIG. 16, the method of placement of the medical device 1500 is described in accordance with an embodiment of the present invention.

In order to describe the methods and surgical processes for placement of a medical device within a bodily passageway, the medical device 1500 is used hereafter. However, it must be appreciated that the medical device 1400 can also be employed and placed in a similar manner.

The method includes placing a first portion such as the first portion 1502 within a body of a patient at step 1702 such that the first portion 1502 is disposed adjacent to a portion of the bodily passageway. The first portion 1502 has been described in conjunction with FIGS. 14 and 15. In this case, an operator can make bodily incisions in perineum, or anteriolateral, posteriolateral or lateral locations with respect to the patient's anus. The operator inserts the tool through any of the incisions and surrounds the first portion 1502 around the bodily passageway firmly. The bodily incisions can finally be sutured. After being placed, the first portion takes a form similar to a ring or loop.

The method further includes placing a second portion such as the second portion 1504 at step 1704 such that the second portion 1504 is disposed adjacent to the first portion 1502. The method of placement of the second portion 1504 can be similar to the method of placement of the first portion 1502 except that it does not surround the bodily passageway completely. Finally, the second portion 1504 is fixed to the first portion 1502 at step 1706. A first end portion such as the first end portion 1510 of the second portion 1504 is coupled to a first end portion such as the first end portion 1506 of the first portion 1502. A second end portion, such as the second end portion 1512 of the second portion 1504, is configured to be coupled to a second end portion such as the second end portion 1508 of the first portion 1504. In some embodiments, the bodily incisions are then closed and sutured.

In some embodiments, a medical device includes a valve member and a securing member. The valve member is configured to be positioned inside a bodily passageway. The valve member has a plurality of flaps configured to move from a first position to a second position at a predetermined pressure. The securing member is configured to be positioned outside the bodily passageway. The securing member is configured to help retain the valve member in place within the bodily passageway.

In some embodiments, the valve member comprises two flaps. In some embodiments, a first flap of the two flaps is configured to contact a second flap of the two flaps to close the valve member when the plurality of flaps are in the first position. In some embodiments, a first flap of the two flaps is configured to separate from a second flap of the two flaps to open the valve member when the plurality of flaps are in the second position. In some embodiments, the valve member is made of an elastomeric material.

In some embodiments, the bodily passageway is at least one of a urethra, an anal canal, and a rectum of a patient. In some embodiments, the predetermined pressure is developed due to an accumulated bodily material inside the bodily passageway. In some embodiments, the accumulated bodily material is a fecal material that is accumulated inside an anal canal of a patient. In some embodiments, the valve member includes a raised portion and the securing member is configured to engage the raised portion of the valve member. In some embodiments, the valve member includes a first raised portion and a second raised portion. The securing member is configured to fit between the first raised portion and the second raised portion of the valve member. In some embodiments, the valve member includes a groove formed circumferentially on an outer surface of the valve member and the securing member is configured to engage within the groove of the valve member.

In some embodiments, a method includes disposing a valve member inside a bodily passageway; and disposing a securing member outside the bodily passageway such that the securing member is configured to engage the valve member to help retain the valve member within the bodily passageway.

In some embodiments, the valve member is made of an elastomeric material. In some embodiments, the bodily passageway is at least one of a urethra, anal canal, and rectum of a patient. In some embodiments, the predetermined pressure is developed due to an accumulated bodily material inside the bodily passageway. In some embodiments, the accumulated bodily material is a fecal material that is accumulated inside an anal canal of a patient.

In some embodiments, the method includes engaging the securing member with a raised portion of the valve member such that the securing member is configured to retain the valve member in place within the bodily passageway.

In some embodiments, the method includes engaging the securing member between a first raised portion and a second raised portion of the valve member such that the securing member is configured to retain the valve member in place within the bodily passageway.

In some embodiments, the method includes engaging the securing member with a groove of the valve member such that the securing member is configured to retain the valve member in place.

In some embodiments, a medical device includes a first portion and a second portion. The first portion is configured to be placed within a body of a patient such that the first portion is disposed adjacent a portion of a bodily passageway. The first portion has a first end portion and a second end portion. The second portion has a first end portion and a second end portion. The first end portion of the second portion is coupled to the first end portion of the first portion. The second end portion of the second portion is coupled to the second end portion of the first portion. The second portion is configured to move from a first length to a second length in response to a predetermined pressure being developed within the bodily passageway.

In some embodiments, the bodily passageway is at least one of a urethra, an anal canal, and a rectum of a patient. In some embodiments, the predetermined pressure is developed due to an accumulated bodily material inside the bodily passageway. In some embodiments, the accumulated bodily material is a fecal material that is accumulated inside an anal canal of a patient. In some embodiments, the first portion is configured to form a ring upon placement inside the bodily passageway. In some embodiments, the second portion comprises a spring. In some embodiments, the second portion is made of nitinol.

While the invention has been disclosed in connection with the preferred embodiments shown and described in detail, various modifications and improvements thereon will become readily apparent to those skilled in the art. Accordingly, the spirit and scope of the present invention is not to be limited by the foregoing examples, but it is to be understood in the broadest sense allowable by law.

What is claimed is:

1. A medical device comprising:
a valve member configured to be positioned inside a bodily passageway, the valve member defining an inlet port for receiving bodily material, the valve member defining an outlet port for outputting the bodily material, the valve member having a plurality of flaps configured to move from a first position in which the bodily material is prevented from flowing out of the outlet port to a second position in which the bodily material is permitted to flow out of the outlet port, the plurality of flaps being configured to move from the first position to the second position when a pressure from the bodily material exceeds a threshold, the plurality of flaps including a first flap and a second flap, the first flap and the second flap being configured to move away from each other when the pressure exceeds the threshold such that an opening is formed between the first flap and the second flap,
the valve member including an upper portion and a lower portion, the upper portion being larger in circumferential area than the lower portion,
the opening being disposed along a portion of a longitudinal axis of the valve member, the opening starting at an edge of the lower portion and extending into the upper portion of the valve member along the portion of the longitudinal axis of the valve member; and a securing member configured to be positioned outside the bodily passageway, the securing member being configured to help retain the valve member in place within the bodily passageway, the upper portion on the valve member including a first raised portion and a second raised portion, the first raised portion being disposed apart from the second raised portion, the first raised portion and the second raised portion being disposed between the inlet port and the outlet portion, the securing member defining a loop, the loop configured to be disposed between the first raised portion and the second raised portion.

2. The medical device of claim 1, wherein the upper portion includes the inlet port, the lower portion includes the outlet port, and a body portion disposed between the upper portion and the lower portion, the upper portion being larger in circumferential area than the lower portion.

3. The medical device of claim 1, wherein the first flap is configured to contact the second flap to close the valve member when the plurality of flaps are in the first position.

4. The medical device of claim 1, wherein the first flap is configured to be engaged with the second flap when in the first position to close the valve member, and the first flap is configured to be separated from the second flap when in the second position to at least partially open the valve member.

5. The medical device of claim 1, wherein the valve member is made of an elastomeric material.

6. The medical device of claim 1, wherein the bodily passageway is at least one of a urethra, an anal canal, and a rectum of a patient.

7. The medical device of claim 1, wherein the threshold is a threshold cracking pressure that develops due to an accumulated bodily material inside the bodily passageway.

8. The medical device of claim 7, wherein the accumulated bodily material is a fecal material that is accumulated inside an anal canal of a patient.

9. A method comprising:
disposing a valve member inside a bodily passageway, the valve member defining an inlet port for receiving bodily material, the valve member defining an outlet port for outputting the bodily material, the valve member having a plurality of flaps including a first flap and a second flap, the valve member closing when the first flap contacts the second flap to prevent the bodily material from flowing out of the outlet port, the valve member including a first raised portion and a second raised portion, the first raised portion being disposed apart from the second raised portion, the first raised portion and the second raised portion being disposed between the inlet port and the outlet portion;

disposing a securing member outside the bodily passageway to engage the valve member and to help retain the valve member within the bodily passageway, the securing member including an elastomeric member being disposed around a circumference of the bodily passageway, the circumference including a portion of an external surface of the bodily passageway, the elastomeric member being disposed between the first raised portion and the second raised portion; and moving the first and second flaps away from each other when a pressure from the bodily material exceeds a threshold to at least partially open the valve member and to permit the bodily material to flow out of the outlet port.

10. The method of claim 9, wherein the valve member is made of an elastomeric material.

11. The method of claim 9, wherein the bodily passageway is at least one of a urethra, anal canal, and rectum of a patient.

12. The method of claim 9, wherein the pressure is developed due to an accumulated bodily material inside the bodily passageway.

13. The method of claim 12, wherein the accumulated bodily material is a fecal material that is accumulated inside an anal canal of a patient.

14. The method of claim 9, further comprising:
moving the first and second flaps towards each other when the pressure falls below the threshold such that the first flap contacts the second flap to close the valve member.

* * * * *